(12) United States Patent
Ademe et al.

(10) Patent No.: US 9,664,570 B2
(45) Date of Patent: May 30, 2017

(54) SYSTEM FOR ANALYZING A SMOKING ARTICLE FILTER ASSOCIATED WITH A SMOKING ARTICLE, AND ASSOCIATED METHOD

(71) Applicant: R.J. Reynolds Tobacco Company, Winston-Salem, NC (US)

(72) Inventors: Balager Ademe, Winston-Salem, NC (US); Gary Lee Wood, Rural Hall, NC (US)

(73) Assignee: R.J. REYNOLDS TOBACCO COMPANY, Winston-Salem, NC (US)

( * ) Notice: Subject to any disclaimer, the term of this patent is extended or adjusted under 35 U.S.C. 154(b) by 342 days.

(21) Appl. No.: 13/675,187

(22) Filed: Nov. 13, 2012

(65) Prior Publication Data

US 2014/0131579 A1    May 15, 2014

(51) Int. Cl.
G01J 5/28       (2006.01)
A24C 5/34      (2006.01)
(Continued)

(52) U.S. Cl.
CPC .............. *G01J 5/28* (2013.01); *A24C 5/3412* (2013.01); *A24D 3/0295* (2013.01); *G01N 21/95* (2013.01); *A24D 3/0216* (2013.01)

(58) Field of Classification Search
CPC ..................... G01N 21/3581; G01N 21/3586
(Continued)

(56) References Cited

U.S. PATENT DOCUMENTS 2,246,107 A    6/1941   Ruau
3,288,147 A    11/1966  Molins et al.
(Continued)

FOREIGN PATENT DOCUMENTS

CN    1276999    12/2000
CN    1468068    1/2004
(Continued)

OTHER PUBLICATIONS

Chan et al., Imaging with terahertz radiation, IOP Publishing, Rep. Prog. Phys. 70 (2007) 1325-1379.*
(Continued)

*Primary Examiner* — David Porta
*Assistant Examiner* — Djura Malevic
(74) *Attorney, Agent, or Firm* — Womble Carlyle Sandridge & Rice, LLP

(57) ABSTRACT

A system and associated method for analyzing a smoking article filter is provided. An emitter emits an initial signal toward a smoking article filter. The initial signal may have a frequency between about 0.1 teraHertz and about 10 teraHertz. A sensor may detect a resultant signal resulting from interaction of the initial signal with the smoking article filter. An analysis unit may receive the resultant signal from the sensor, determine a filter status based on the resultant signal, and output an indicium indicative of the filter status. The filter status may include a capsule presence within the smoking article filter, a capsule absence from the smoking article filter, a proper insertion of a capsule into the smoking article filter, a defective insertion of a capsule into the smoking article filter, a proper capsule within the smoking article filter, and a defective capsule within the smoking article filter.

19 Claims, 11 Drawing Sheets

(51) Int. Cl.
  *G01N 21/95* (2006.01)
  *A24D 3/02* (2006.01)
(58) Field of Classification Search
  USPC .... 250/341.1, 338.1, 353, 339.1, 341.2, 342
  See application file for complete search history.

(56) References Cited

U.S. PATENT DOCUMENTS

| | | |
|---|---|---|
| 3,301,454 A | 1/1967 | Wayne et al. |
| 3,308,600 A | 3/1967 | Erdmann et al. |
| 3,366,121 A | 1/1968 | Carty |
| 3,398,675 A | 8/1968 | Potter et al. |
| 3,424,172 A | 1/1969 | Neurath |
| 3,428,049 A | 2/1969 | Leake et al. |
| 3,444,517 A | 5/1969 | Rabinow |
| 3,550,508 A | 12/1970 | Wartman, Jr. |
| 3,550,598 A | 12/1970 | McGlumphy et al. |
| 3,575,276 A | 4/1971 | Rupert |
| 3,602,231 A | 8/1971 | Dock |
| 3,685,521 A | 8/1972 | Dock |
| 3,818,223 A | 6/1974 | Gibson et al. |
| 3,884,246 A | 5/1975 | Walker |
| 3,915,176 A | 10/1975 | Heitmann et al. |
| 4,053,056 A | 10/1977 | Day |
| 4,083,460 A | 4/1978 | Venturi |
| 4,171,739 A | 10/1979 | Yamato |
| 4,174,719 A | 11/1979 | Martin et al. |
| 4,238,993 A | 12/1980 | Brand et al. |
| 4,280,187 A | 7/1981 | Reuland et al. |
| 4,281,670 A | 8/1981 | Heitmann et al. |
| 4,281,671 A | 8/1981 | Bynre et al. |
| 4,284,088 A | 8/1981 | Brand et al. |
| 4,291,713 A | 9/1981 | Frank |
| 4,294,353 A | 10/1981 | Focke et al. |
| RE30,964 E | 6/1982 | Butner et al. |
| 4,403,620 A | 9/1983 | Joseph et al. |
| 4,445,520 A | 5/1984 | Knight et al. |
| 4,474,190 A | 10/1984 | Brand |
| 4,534,463 A | 8/1985 | Bouchard |
| 4,574,816 A | 3/1986 | Rudszinat |
| 4,715,497 A | 12/1987 | Focke et al. |
| 4,736,754 A | 4/1988 | Heitmann et al. |
| 4,776,466 A | 10/1988 | Yoshida |
| 4,781,203 A | 11/1988 | La Hue |
| 4,807,809 A | 2/1989 | Pryor et al. |
| 4,811,745 A | 3/1989 | Cohen et al. |
| 4,844,100 A | 7/1989 | Holznagel |
| 4,850,301 A | 7/1989 | Greene, Jr. et al. |
| 4,852,734 A | 8/1989 | Allen et al. |
| 4,862,905 A | 9/1989 | Green, Jr. et al. |
| 4,878,506 A | 11/1989 | Pinck et al. |
| 4,889,144 A | 12/1989 | Tateno et al. |
| 4,920,990 A | 5/1990 | Lawrence et al. |
| 4,925,602 A | 5/1990 | Hill et al. |
| 5,012,823 A | 5/1991 | Keritsis et al. |
| 5,012,829 A | 5/1991 | Thesing et al. |
| 5,025,814 A | 6/1991 | Raker |
| 5,046,111 A | 9/1991 | Cox et al. |
| 5,060,664 A | 10/1991 | Siems et al. |
| 5,060,665 A | 10/1991 | Heitmann |
| 5,061,063 A | 10/1991 | Casasent |
| 5,074,320 A | 12/1991 | Jones, Jr. et al. |
| 5,101,609 A | 4/1992 | Cook |
| 5,101,839 A | 4/1992 | Jakob et al. |
| 5,105,838 A | 4/1992 | White et al. |
| 5,131,416 A | 7/1992 | Gentry |
| 5,139,140 A | 8/1992 | Burrows et al. |
| 5,156,169 A | 10/1992 | Holmes et al. |
| 5,159,944 A | 11/1992 | Arzonico et al. |
| 5,167,244 A | 12/1992 | Kjerstad |
| 5,191,906 A | 3/1993 | Myracle, Jr. |
| 5,220,930 A | 6/1993 | Gentry |
| 5,225,277 A | 7/1993 | Takegawa et al. |
| 5,240,117 A | 8/1993 | Focke et al. |
| 5,271,419 A | 12/1993 | Arzonico et al. |
| 5,333,729 A | 8/1994 | Wolfe |
| 5,353,357 A | 10/1994 | Longest et al. |
| 5,360,023 A | 11/1994 | Blakley et al. |
| 5,387,285 A | 2/1995 | Rivers |
| 5,396,909 A | 3/1995 | Gentry et al. |
| 5,432,600 A | 7/1995 | Grollimund et al. |
| 5,472,002 A | 12/1995 | Covarrubias |
| 5,476,108 A | 12/1995 | Dominguez et al. |
| 5,515,159 A | 5/1996 | Sites et al. |
| 5,542,901 A | 8/1996 | Atwell et al. |
| 5,588,068 A | 12/1996 | Longest et al. |
| 5,660,382 A | 8/1997 | Meier |
| 5,718,250 A | 2/1998 | Banerjee et al. |
| 5,740,902 A | 4/1998 | Spatafora |
| 5,875,824 A | 3/1999 | Atwell et al. |
| 5,898,104 A | 4/1999 | Rohrssen et al. |
| 5,938,018 A | 8/1999 | Keaveney et al. |
| 5,977,780 A | 11/1999 | Herrmann |
| 6,020,969 A | 2/2000 | Struckhoff et al. |
| 6,054,665 A | 4/2000 | Focke et al. |
| 6,117,455 A | 9/2000 | Takada et al. |
| 6,158,193 A | 12/2000 | Focke et al. |
| 6,213,128 B1 | 4/2001 | Smith et al. |
| 6,229,115 B1 | 5/2001 | Voss et al. |
| 6,246,778 B1 | 6/2001 | Moore |
| 6,360,751 B1 | 3/2002 | Fagg et al. |
| 6,384,359 B1 | 5/2002 | Belcastro et al. |
| 6,385,333 B1 | 5/2002 | Puckett et al. |
| 6,437,317 B1 | 8/2002 | Focke et al. |
| 6,537,186 B1 | 3/2003 | Veluz |
| 6,612,429 B2 | 9/2003 | Dennen |
| 6,647,878 B2 | 11/2003 | Blau et al. |
| 6,726,006 B1 | 4/2004 | Funderburk et al. |
| 6,736,261 B1 | 5/2004 | Thomas et al. |
| 6,761,174 B2 | 7/2004 | Jupe et al. |
| 6,779,530 B2 | 8/2004 | Kraker |
| 6,813,961 B2 | 11/2004 | Stiller et al. |
| 6,848,449 B2 | 2/2005 | Kitao et al. |
| 6,904,917 B2 | 6/2005 | Kitao et al. |
| 7,074,170 B2 | 7/2006 | Lanier, Jr. et al. |
| 7,115,085 B2 | 10/2006 | Deal |
| 7,210,486 B2 | 5/2007 | Hartmann |
| 7,234,471 B2 | 6/2007 | Fitzgerald et al. |
| 7,237,559 B2 | 7/2007 | Ashcraft et al. |
| 7,240,678 B2 | 7/2007 | Crooks et al. |
| 7,275,548 B2 | 10/2007 | Hancock et al. |
| 7,281,540 B2 | 10/2007 | Barnes et al. |
| 7,296,578 B2 | 11/2007 | Read, Jr. |
| 7,325,382 B2 | 2/2008 | Nelson et al. |
| 7,434,585 B2 | 10/2008 | Holmes |
| 7,479,098 B2 | 1/2009 | Thomas et al. |
| 7,565,818 B2 | 7/2009 | Thomas et al. |
| 7,578,298 B2 | 8/2009 | Karles et al. |
| 7,654,945 B2 | 2/2010 | Deal |
| 7,740,019 B2 | 6/2010 | Nelson et al. |
| 7,744,922 B2 | 6/2010 | Mane et al. |
| 7,784,356 B2 | 8/2010 | Spiers et al. |
| 7,833,146 B2 | 11/2010 | Deal |
| 7,836,895 B2 | 11/2010 | Dube et al. |
| 7,861,728 B2 | 1/2011 | Holton, Jr. et al. |
| 7,972,254 B2 | 7/2011 | Stokes et al. |
| 8,142,339 B2 | 3/2012 | Deal |
| 8,186,359 B2 | 5/2012 | Ademe et al. |
| 8,262,550 B2 | 9/2012 | Barnes et al. |
| 8,308,623 B2 | 11/2012 | Nelson et al. |
| 2001/0032932 A1 | 10/2001 | Focke |
| 2002/0185141 A1 | 12/2002 | Heide |
| 2003/0136419 A1 | 7/2003 | Muller |
| 2003/0137312 A1 | 7/2003 | Cerati et al. |
| 2003/0145866 A1 | 8/2003 | Hartmann |
| 2003/0178036 A1 | 9/2003 | Demmer et al. |
| 2003/0206023 A1 | 11/2003 | Herrmann |
| 2004/0129281 A1 | 7/2004 | Hancock et al. |
| 2004/0141174 A1 | 7/2004 | Focke et al. |
| 2004/0217023 A1 | 11/2004 | Fagg et al. |
| 2004/0256253 A1 | 12/2004 | Henson et al. |
| 2004/0261807 A1 | 12/2004 | Dube et al. |
| 2005/0016556 A1 | 1/2005 | Ashcraft et al. |
| 2005/0039764 A1 | 2/2005 | Barnes et al. |

(56) References Cited

U.S. PATENT DOCUMENTS

| | | |
|---|---|---|
| 2005/0066986 A1 | 3/2005 | Nestor et al. |
| 2005/0075754 A1 | 4/2005 | Zeitler et al. |
| 2005/0076929 A1 | 4/2005 | Fitzgerald et al. |
| 2005/0112228 A1 | 5/2005 | Smith et al. |
| 2005/0150786 A1 | 7/2005 | Mitten et al. |
| 2006/0169295 A1 | 8/2006 | Draghetti |
| 2006/0207616 A1 | 9/2006 | Hapke et al. |
| 2006/0243611 A1 | 11/2006 | Wu |
| 2006/0272655 A1 | 12/2006 | Thomas et al. |
| 2007/0056600 A1 | 3/2007 | Coleman, III et al. |
| 2007/0091326 A1 | 4/2007 | Schroeder et al. |
| 2007/0102015 A1 | 5/2007 | Villarinho |
| 2007/0144542 A1* | 6/2007 | Bencivenni et al. .... A24C 5/34 131/58 |
| 2007/0215167 A1 | 9/2007 | Crooks et al. |
| 2007/0229094 A1 | 10/2007 | Kasai et al. |
| 2007/0246055 A1 | 10/2007 | Oglesby |
| 2008/0029118 A1 | 2/2008 | Nelson et al. |
| 2008/0093234 A1 | 4/2008 | Jones et al. |
| 2008/0099353 A1 | 5/2008 | Parsons et al. |
| 2008/0142028 A1 | 6/2008 | Fagg |
| 2008/0179204 A1 | 7/2008 | Lutzig |
| 2008/0202540 A1 | 8/2008 | Carter et al. |
| 2009/0050163 A1 | 2/2009 | Hartmann et al. |
| 2009/0066948 A1 | 3/2009 | Karpowicz et al. |
| 2009/0090372 A1 | 4/2009 | Thomas et al. |
| 2009/0120449 A1 | 5/2009 | Tindall |
| 2009/0194118 A1 | 8/2009 | Ademe et al. |
| 2010/0059069 A1 | 3/2010 | Boldrini |
| 2010/0059074 A1 | 3/2010 | Brantley et al. |
| 2010/0101589 A1 | 4/2010 | Nelson et al. |
| 2010/0184576 A1 | 7/2010 | Prestia et al. |
| 2010/0236561 A1 | 9/2010 | Barnes et al. |
| 2010/0293106 A1 | 11/2010 | Rhoads et al. |
| 2010/0294290 A1 | 11/2010 | Zhang |
| 2011/0053745 A1 | 3/2011 | Iliev et al. |
| 2011/0067976 A1 | 3/2011 | Pelagatti |
| 2011/0162662 A1 | 7/2011 | Nikolov et al. |
| 2011/0162665 A1 | 7/2011 | Burov et al. |
| 2011/0169942 A1 | 7/2011 | Brantley et al. |
| 2011/0230320 A1 | 9/2011 | Stokes et al. |
| 2011/0271968 A1 | 11/2011 | Carpenter et al. |
| 2012/0037546 A1 | 2/2012 | Dixon et al. |
| 2012/0055493 A1 | 3/2012 | Novak, III et al. |
| 2012/0077658 A1 | 3/2012 | Nikolov et al. |
| 2012/0080043 A1 | 4/2012 | Naenen et al. |
| 2012/0120229 A1 | 5/2012 | Brantley et al. |
| 2012/0245006 A1 | 9/2012 | Henley et al. |
| 2012/0245007 A1 | 9/2012 | Henley et al. |
| 2013/0085052 A1 | 4/2013 | Novak, III et al. |
| 2013/0096711 A1 | 4/2013 | Gates et al. |
| 2014/0263408 A1 | 9/2014 | Amiss |

FOREIGN PATENT DOCUMENTS

| | | |
|---|---|---|
| CN | 1642724 | 7/2005 |
| CN | 1882256 A | 12/2006 |
| CN | 1939165 | 4/2007 |
| CN | 101257809 | 9/2008 |
| CN | 101377406 A | 3/2009 |
| CN | 102131409 A | 7/2011 |
| DE | 10238906 | 3/2004 |
| DE | 10 2008 062 370 | 6/2010 |
| EP | 0 292 949 A2 | 11/1988 |
| EP | 0 704 172 | 4/1996 |
| EP | 1649764 A1 | 4/2004 |
| EP | 1 669 755 | 6/2006 |
| EP | 1 754 419 A1 | 2/2007 |
| EP | 1 767 107 | 3/2007 |
| EP | 1 916 188 | 4/2008 |
| EP | 2 031 374 | 3/2009 |
| EP | 2 042 855 | 4/2009 |
| EP | 2 243 384 A1 | 10/2010 |
| EP | 2243385 A2 | 10/2010 |
| EP | 2 338 797 A1 | 6/2011 |
| GB | 1058343 A2 | 2/1967 |
| GB | 2 020 158 | 11/1979 |
| GB | 1042000 | 9/1996 |
| JP | 9325123 | 12/1997 |
| JP | 2001-190262 | 7/2001 |
| JP | 2003-219855 | 8/2003 |
| JP | 2004-504825 | 2/2004 |
| WO | WO 01/79092 | 10/2001 |
| WO | WO 03/009711 | 2/2003 |
| WO | WO 03/047836 | 6/2003 |
| WO | WO 03/082558 | 10/2003 |
| WO | WO 2004/083834 A1 | 9/2004 |
| WO | WO 2005/113386 | 12/2005 |
| WO | WO 2006/064371 | 6/2006 |
| WO | WO 2006/092962 | 9/2006 |
| WO | WO 2007/028957 | 3/2007 |
| WO | WO 2007/038053 | 4/2007 |
| WO | WO 2009/156468 | 12/2009 |
| WO | WO 2013/145163 | 10/2013 |

OTHER PUBLICATIONS

Davis et al., *Tobacco Production, Chemistry and Technology*, 1999, pp. 440-460, Blackwell Science, Inc., Malden, MA.

Johnson, *Development of Cigarette Components to Meet Industry Needs*, 52$^{nd}$ T.S.R.C., Sep. 1998.

International Search Report and Written Opinion of the International Searching Authority for corresponding International Application No. PCT/US2013/069627 mailed Mar. 13, 2014.

U.S. Appl. No. 13/275,016, filed Oct. 17, 2011, Gates et al.

U.S. Appl. No. 13/248,847, filed Sep. 29, 2011, Novak III, et al.

mini-Z™ Terahertz Time Domain Spectrometer Brochure http://dl.z-thz.com/brochures/mini-ZRev5.pdf downloaded from website on Jan. 16, 2013.

* cited by examiner

SYSTEM FOR ANALYZING A SMOKING ARTICLE FILTER ASSOCIATED WITH A SMOKING ARTICLE, AND ASSOCIATED METHOD

BACKGROUND

Field of the Disclosure

The present disclosure relates to products made or derived from tobacco, or that otherwise incorporate tobacco, and are intended for human consumption and methods for the production thereof. In this regard, embodiments of the present disclosure relate to the manufacture of filter rods and smoking articles incorporating such filter rods and, more particularly, to systems and methods for analyzing a smoking article filter associated with a smoking article, such as a cigarette, for determining a filter status with respect thereto.

Description of Related Art

Popular smoking articles, such as cigarettes, have a substantially cylindrical rod shaped structure and include a charge, roll or column of smokable material such as shredded tobacco (e.g., in cut filler form) surrounded by a paper wrapper thereby forming a so-called "smokable rod" or "tobacco rod." Normally, a cigarette has a cylindrical filter element aligned in an end-to-end relationship with the tobacco rod. Typically, a filter element comprises cellulose acetate tow plasticized using triacetin, and the tow is circumscribed by a paper material known as "plug wrap." A cigarette can incorporate a filter element having multiple segments, and one of those segments can comprise activated charcoal particles. Typically, the filter element is attached to one end of the tobacco rod using a circumscribing wrapping material known as "tipping paper." It also has become desirable in some embodiments to perforate the tipping material and plug wrap, in order to provide dilution of drawn mainstream smoke with ambient air. Descriptions of cigarettes and the various components thereof are set forth in Tobacco Production, Chemistry and Technology, Davis et al. (Eds.) (1999). A cigarette is employed by a smoker by lighting one end thereof and burning the tobacco rod. The smoker then receives mainstream smoke into his/her mouth by drawing on the opposite end (e.g., the filter end) of the cigarette.

Various ways to alter the characteristics of mainstream smoke (including ways to enhance the sensory aspects of that smoke), and various devices suitable for producing components of smoking articles incorporating objects such as breakable flavor-containing capsules also are set forth in the background art of U.S. Pat. No. 8,186,359 to Ademe et al., which is incorporated herein by reference in its entirety. Furthermore, various devices suitable for producing components of smoking articles incorporating objects, such as breakable capsules, also are set forth in the background art of U.S. Pat. No. 8,186,359 to Ademe et al. See also, for example, the types of cigarettes, cigarette components and cigarette component manufacturing devices set forth in U.S. Patent Application Publication Nos. 2009/0050163 to Hartmann et al.; 2010/010589 to Nelson et al.; 2010/0294290 to Zhang; 2010/0184576 to Prestia et al.; 2011/0162662 to Nikolov et al.; 2011/0162665 to Burov et al.; 2011/0169942 to Brantley et al.; 2011/0271968 to Carpenter et al.; 2012/0245006 to Henley et al. and 2012/0245007 to Henley et al.; which are incorporated herein by reference in their entireties.

Typically, cigarettes incorporating breakable capsules have those capsules positioned within the filter elements of those cigarettes. During the manufacturing process of those filter elements, filter material is formed into a continuous rod having the breakable capsules positioned within a continuous rod along the longitudinal axis thereof. The continuous rod then is subdivided at predetermined intervals so as to form a plurality of filter rods or rod portions, such that each rod portion has one or more breakable capsules positioned therein. Manners and methods for inspecting breakable capsules within filter rods during filter rod manufacture have been set forth in U.S. Pat. No. 8,186,359 to Ademe et al. and U.S. Patent Application Publication No. 2011/0169942 to Brantley et al. However, it would be desirable to inspect breakable capsules within cigarette components at various stages of the cigarette manufacturing process with improved accuracy. As such, there exists a need for an inspection/detection system having enhanced sensing capabilities.

BRIEF SUMMARY

The above and other needs are addressed by the present disclosure which, in particular aspects, relates to a system and process for detecting and inspecting one or more objects (e.g., rupturable capsules, pellets, strands, or combinations thereof) inserted into and disposed within a filter element or along the length of a filter rod, each associated with a smoking article.

In one aspect, a system is provided. The system may include an emitter configured to emit an initial signal, having a frequency between about 0.1 teraHertz and about 10 teraHertz, toward a smoking article filter, a sensor configured to detect a resultant signal resulting from interaction of the initial signal with the smoking article filter, and an analysis unit configured to receive the resultant signal from the sensor, determine a filter status based on the resultant signal, and output an indicium indicative of the filter status.

In one embodiment the sensor and the emitter may be configured to receive the smoking article filter therebetween. A converging lens may be configured to focus the initial signal perpendicularly to a longitudinal axis of the smoking article filter and a collimator lens may be configured to substantially straighten the resultant signal. At least one of the converging lens and the collimator lens may comprise polymethylpentene.

In some embodiments the system may further comprise a movement apparatus configured to at least one of linearly displace the smoking article filter along a longitudinal axis thereof and rotate the smoking article filter about the longitudinal axis relative to the sensor and the emitter. The analysis unit may be configured to determine at least one of a transmission time of the resultant signal and an amplitude of the resultant signal. The analysis unit may be further configured to determine at least one of a difference between the transmission time of the resultant signal and a transmission time of a reference signal and a difference between the amplitude of the resultant signal and the amplitude of the reference signal.

In some embodiments the frequency of the initial signal may be about 0.48 teraHertz. Further, the filter status may comprise at least one of a capsule presence within the smoking article filter, a capsule absence from the smoking article filter, a proper insertion of a capsule into the smoking article filter, a defective insertion of a capsule into the smoking article filter, a proper capsule within the smoking article filter, and a defective capsule within the smoking article filter. The system may also include a rod-making apparatus including a capsule insertion unit configured to insert a capsule into the smoking article filter, wherein the sensor and the emitter may be disposed downstream from the capsule insertion unit. The sensor and the emitter may additionally be positioned downstream of a tipping device configured to wrap a tipping material around the smoking article filter and a tobacco rod. The system may further comprise a defective smoking article filter removal device in communication with the analysis unit and configured to remove a defective smoking article filter when the filter status indicates at least one of a capsule absence from the smoking article filter, a defective insertion of a capsule into the smoking article filter, and a defective capsule within the smoking article filter.

In an additional aspect, a method is provided. The method may comprise emitting an initial signal having a frequency between about 0.1 teraHertz and about 10 teraHertz toward a smoking article filter, detecting a resultant signal resulting from interaction of the initial signal with the smoking article filter, determining a filter status based on the resultant signal, and outputting an indicium indicative of the filter status.

In some embodiments the method may further comprise positioning the smoking article filter between the sensor and the emitter. Additionally, the method may include focusing the initial signal perpendicularly to a longitudinal axis of the smoking article filter and straightening the resultant signal. The method may also include at least one of linearly displacing the smoking article filter along a longitudinal axis thereof and rotating the smoking article filter about the longitudinal axis.

In some embodiments determining the filter status may comprise at least one of determining a transmission time of the resultant signal and determining an amplitude of the resultant signal. Additionally, determining the filter status may comprise at least one of determining a difference between the transmission time of the resultant signal and a transmission time of a reference signal and determining a difference between the amplitude of the resultant signal and the amplitude of the reference signal.

In some embodiments the frequency of the initial signal may be about 0.48 teraHertz. Further, the filter status may comprise at least one of a capsule presence within the smoking article filter, a capsule absence from the smoking article filter, a proper insertion of a capsule into the smoking article filter, a defective insertion of a capsule into the smoking article filter, a proper capsule within the smoking article filter, and a defective capsule within the smoking article filter. The method may also include inserting a capsule into the smoking article filter, wherein emitting the initial signal and detecting the resultant signal occur after inserting the capsule into the smoking article filter. Additionally, the method may include wrapping a tipping material around the smoking article filter and a tobacco rod, wherein emitting the initial signal and detecting the resultant signal occur after wrapping the tipping material around the smoking article filter and the tobacco rod. The method may also include removing a defective smoking article filter when the filter status indicates at least one of a capsule absence from the smoking article filter, a defective insertion of a capsule into the smoking article filter, and a defective capsule within the smoking article filter.

Aspects of the present disclosure thus provide significant advantages as otherwise detailed herein.

BRIEF DESCRIPTION OF THE SEVERAL VIEWS OF THE DRAWING(S)

Having thus described the disclosure in general terms, reference will now be made to the accompanying drawings, which are not necessarily drawn to scale, and wherein:

Figure 3:
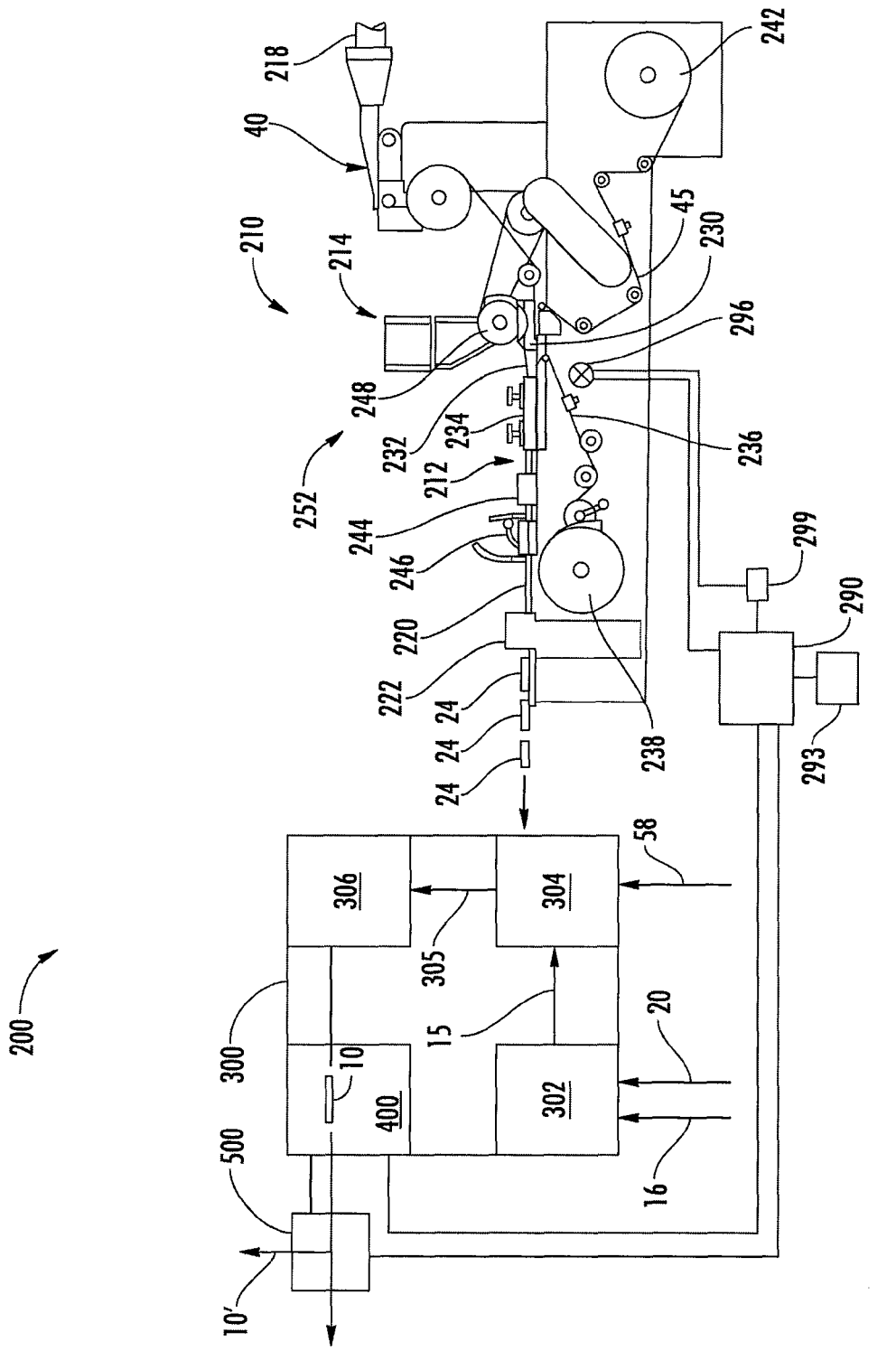
Figure 4:
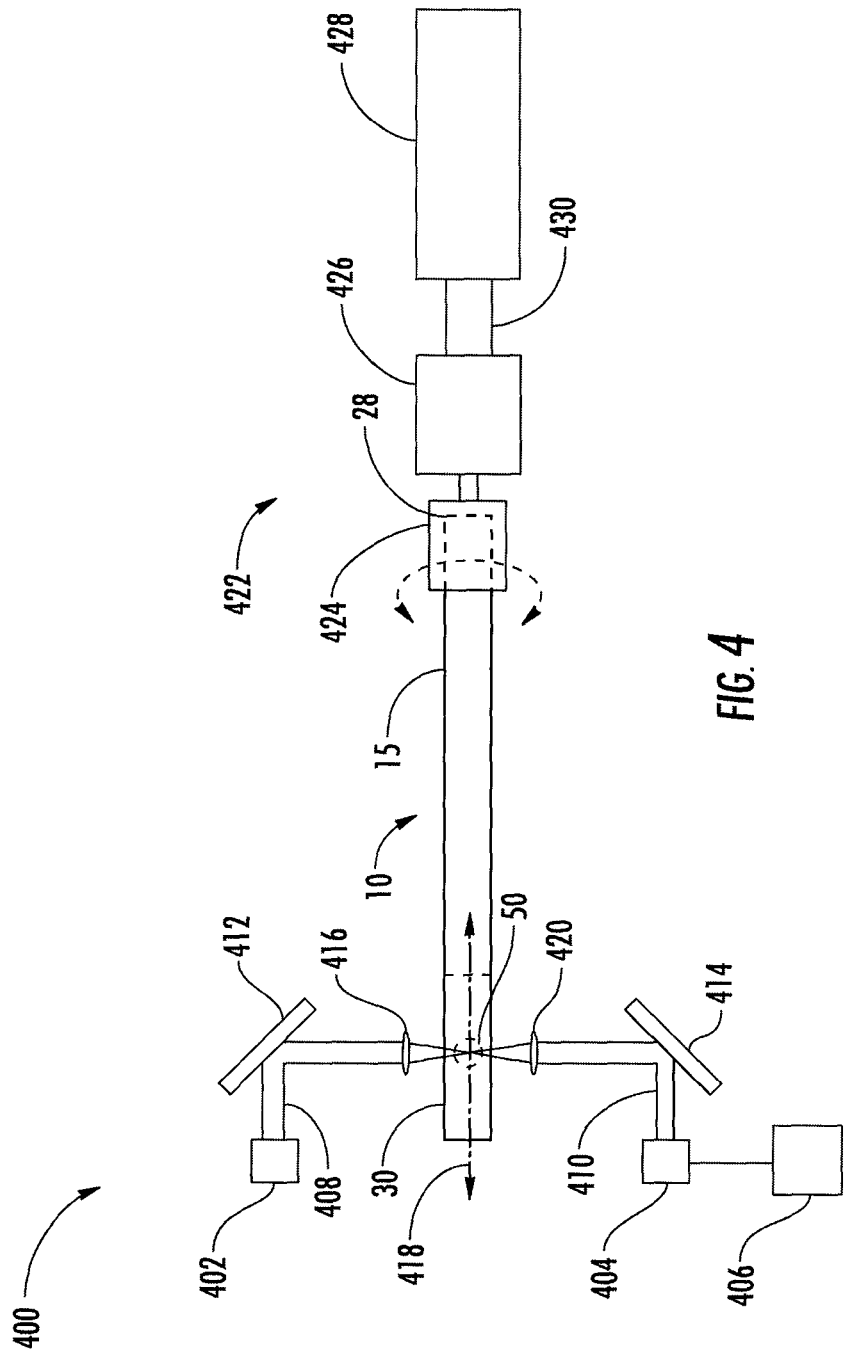
Figure 5:
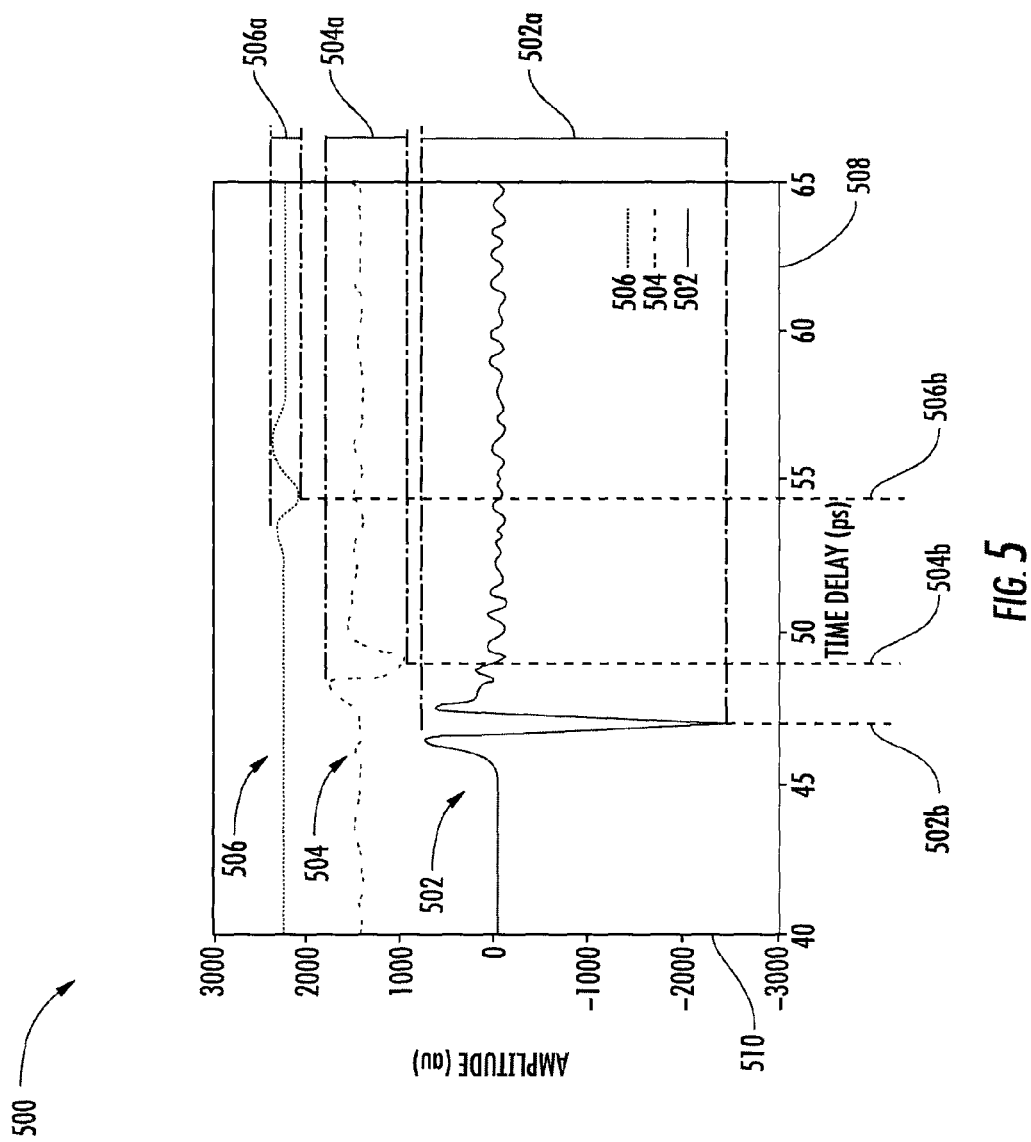
Figure 6:
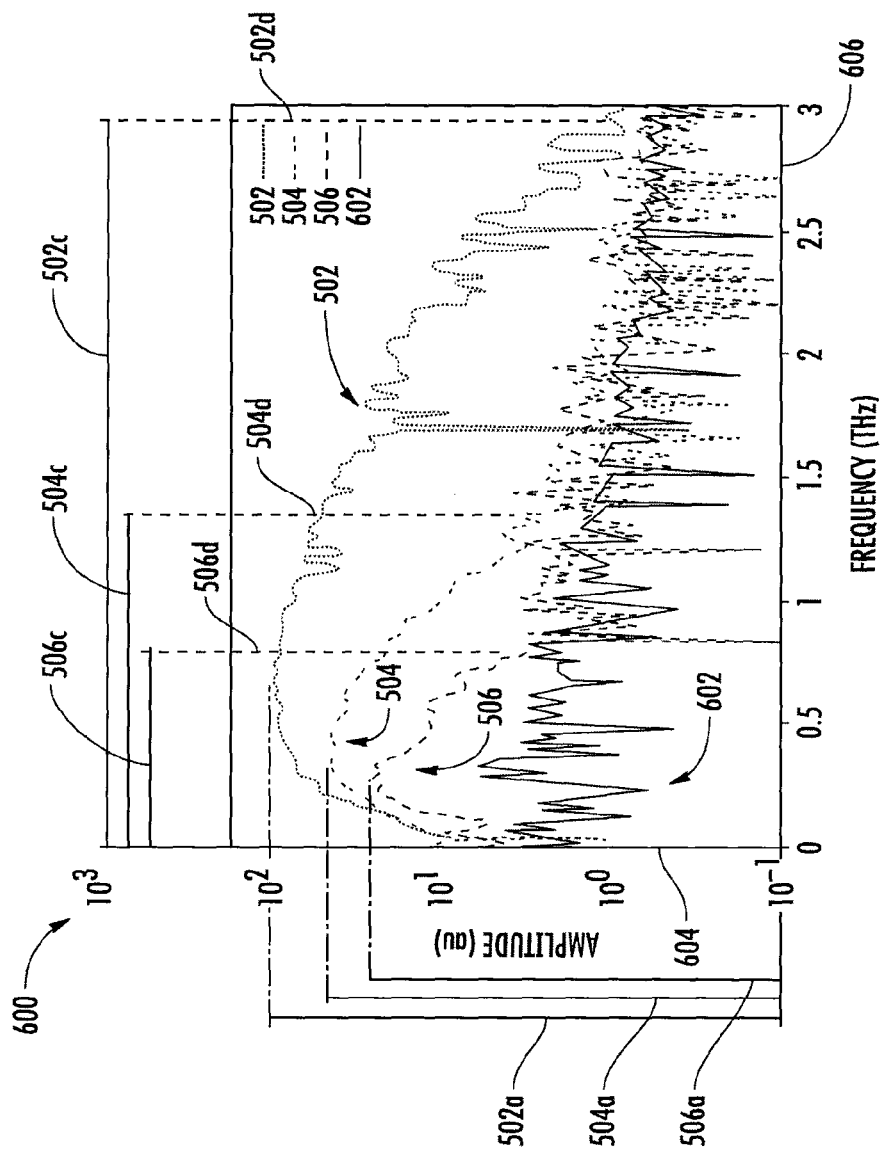
Figure 7:
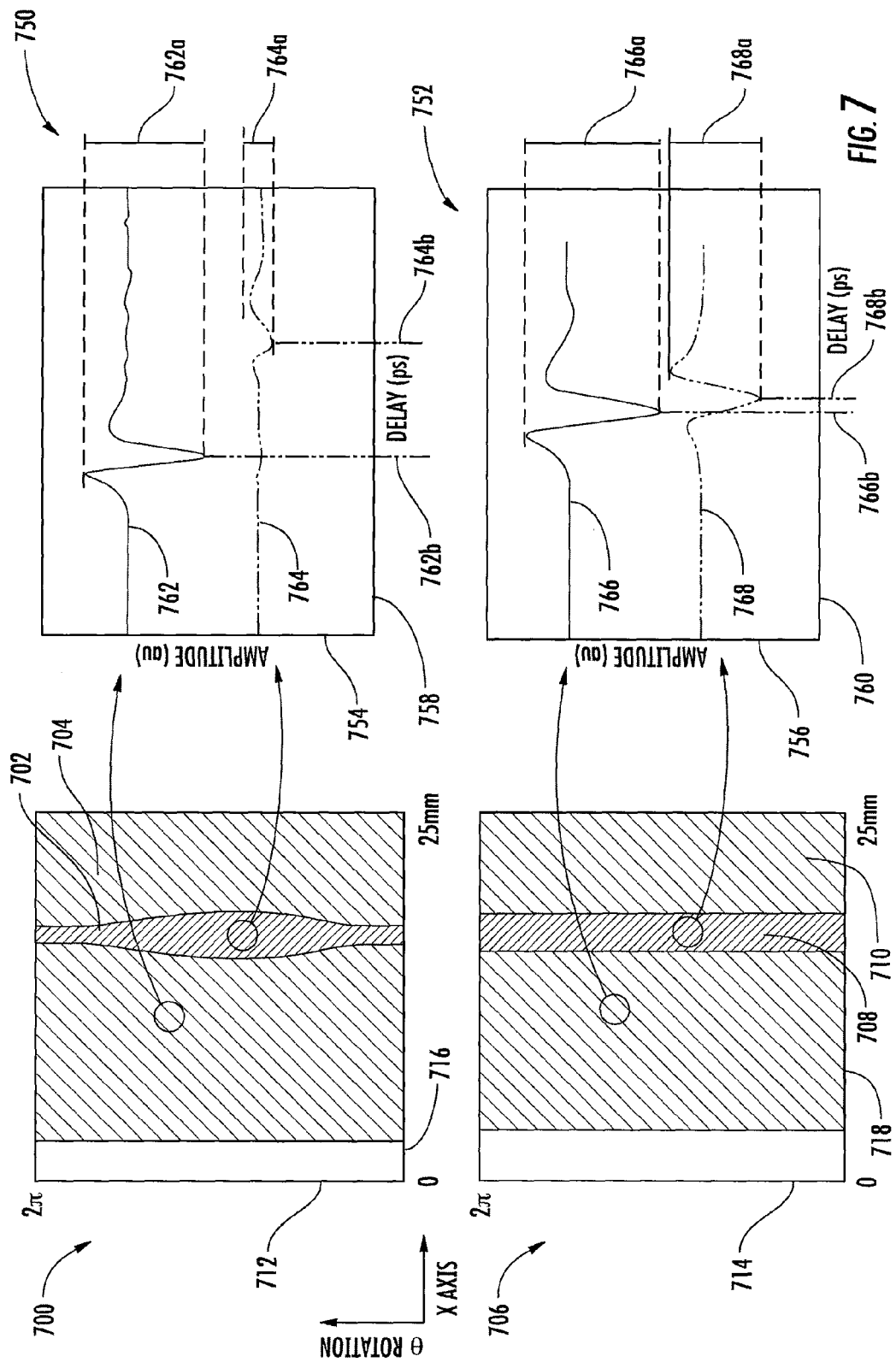
Figure 8:
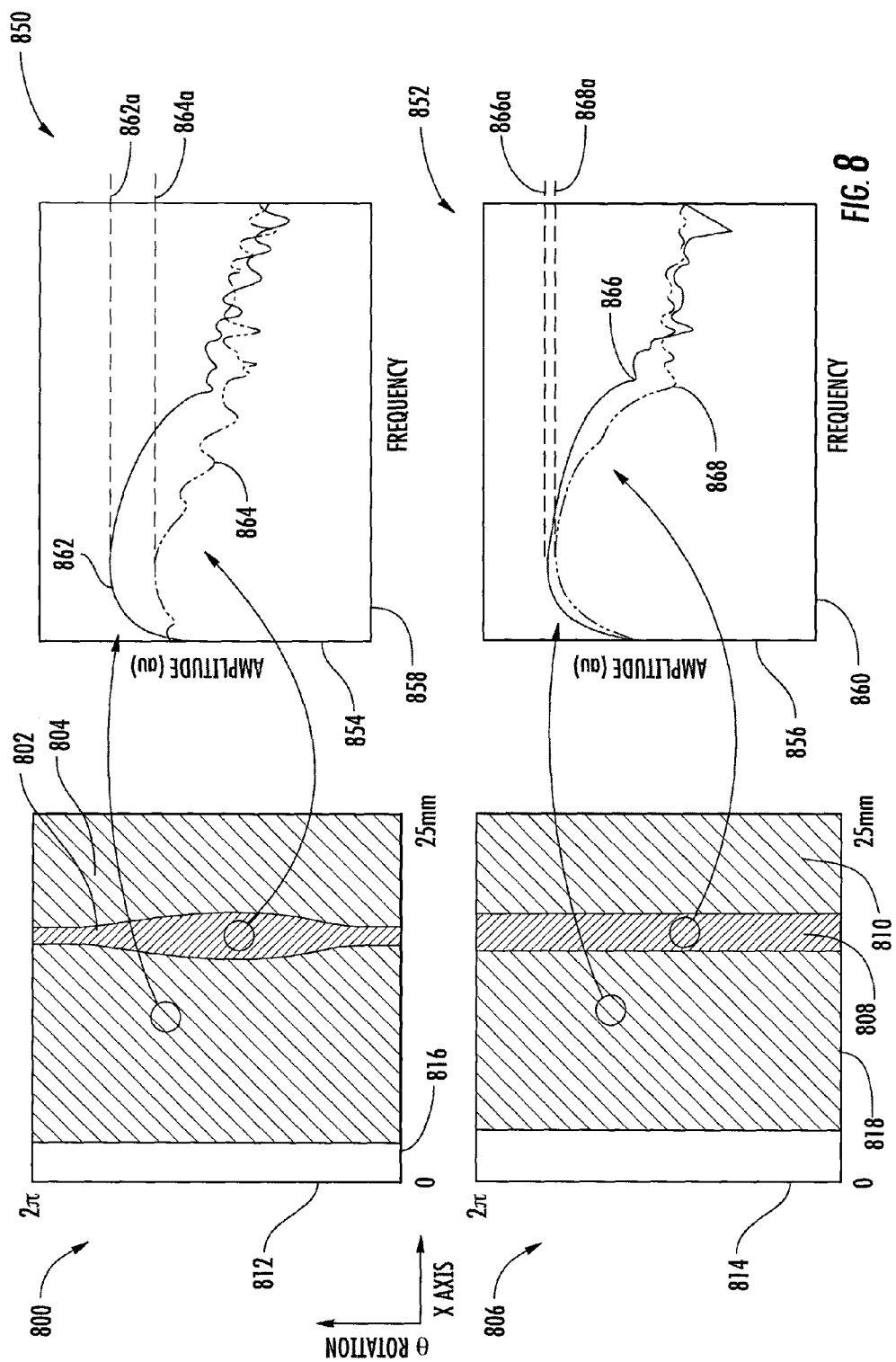
Figure 9:
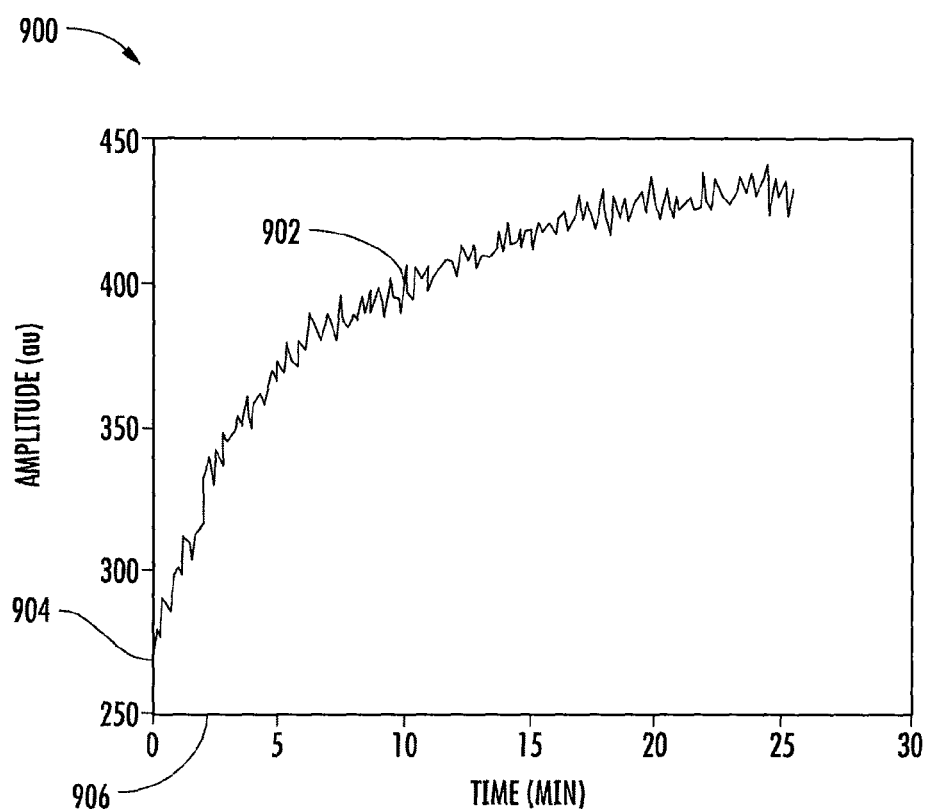
Figure 10:
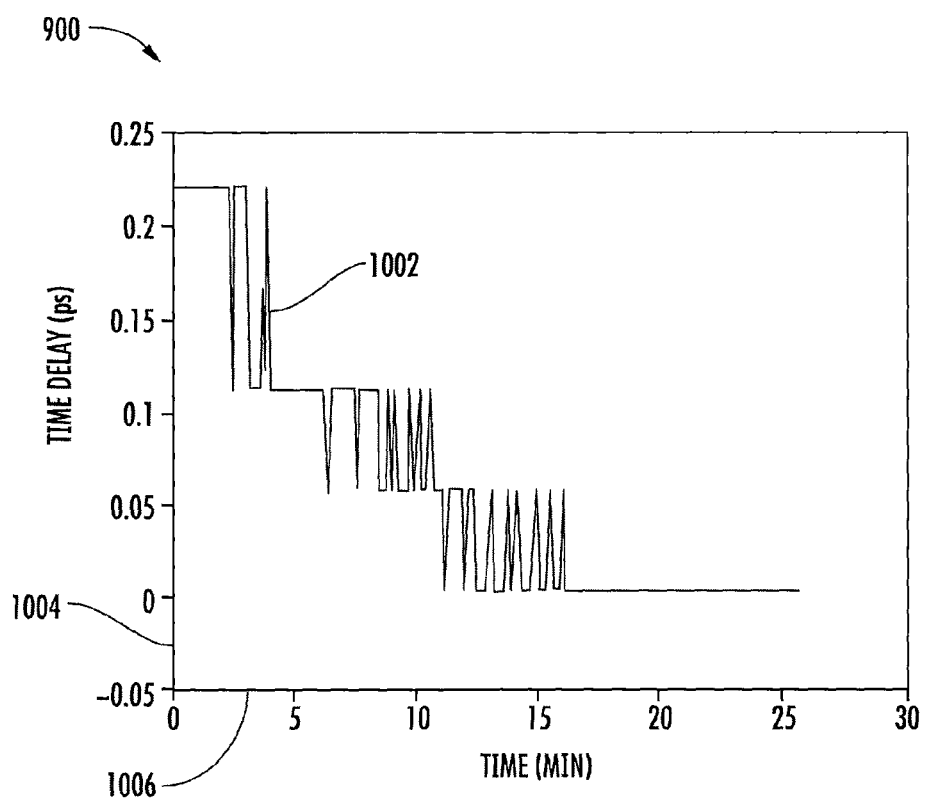
Figure 11:
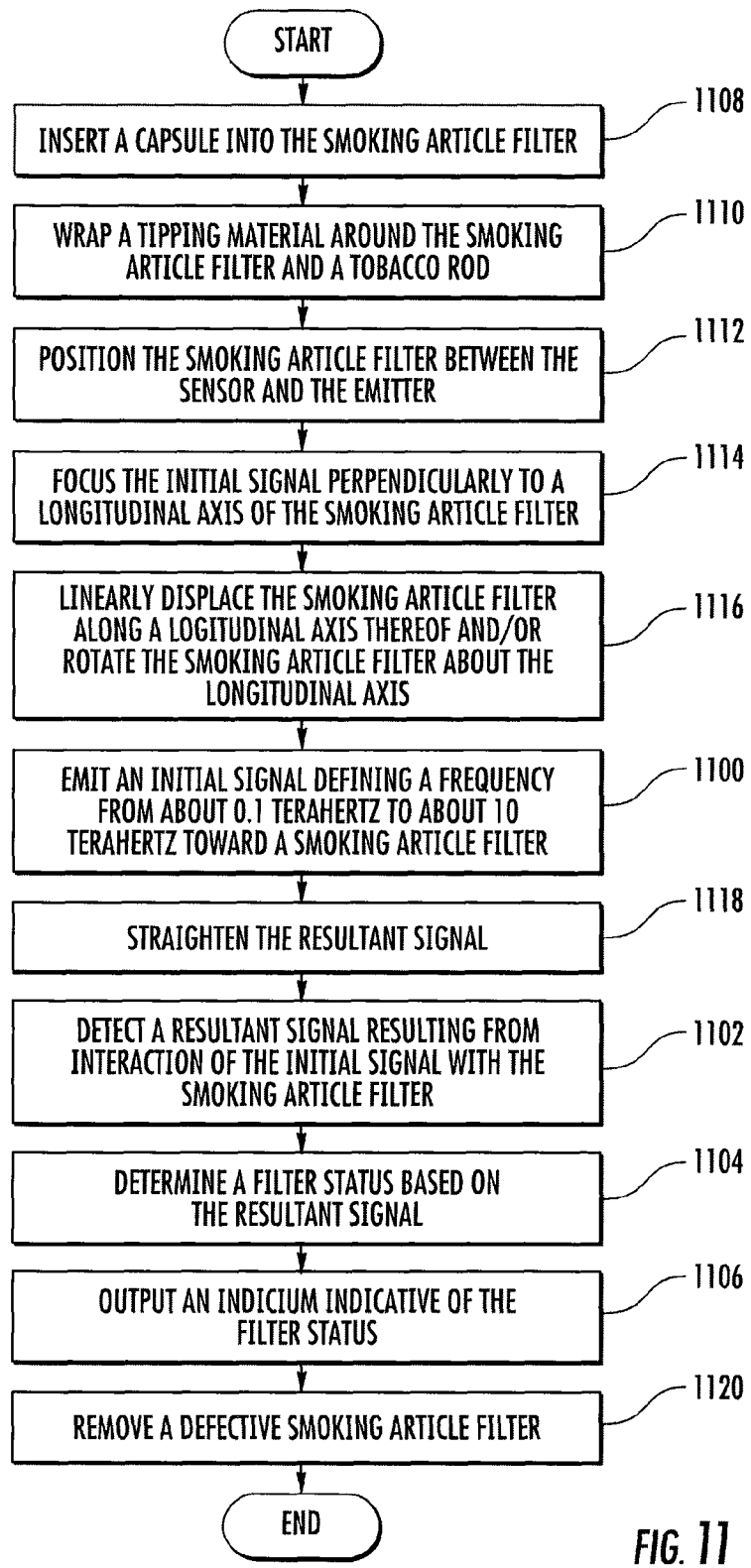

FIG. 3 schematically illustrates a system for forming smoking articles including a rod-making apparatus, a cigarette making apparatus, an inspection/detection system, and a defective smoking article removal device according to an example embodiment of the present disclosure;

FIG. 4 illustrates components of the inspection/detection system of FIG. 3 according to an example embodiment of the present disclosure;

FIG. 5 illustrates a graph of the amplitude versus signal time delay of resultant signals from a filter material and an object and a reference signal according to an example embodiment of the present disclosure;

FIG. 6 illustrates a graph of the amplitude versus frequency of resultant signals from a filter material and an object and a reference signal according to an example embodiment of the present disclosure;

FIG. 7 illustrates images of filter materials with intact and broken objects and graphs of amplitude versus signal time delay of resultant signals associated therewith according to an example embodiment of the present disclosure;

FIG. 8 illustrates images of filter materials with intact and broken objects and graphs of amplitude versus frequency of resultant signals associated therewith according to an example embodiment of the present disclosure;

FIG. 9 illustrates a graph of amplitude of a resultant signal associated with a recently punctured object over time according to an example embodiment of the present disclosure;

FIG. 10 illustrates a graph of signal time delay of a resultant signal associated with a recently punctured object over time according to an example embodiment of the present disclosure; and FIG. 11 illustrates a method for determining a filter status according to an example embodiment of the present disclosure.

DETAILED DESCRIPTION OF THE PREFERRED EMBODIMENTS

The present disclosure now will be described more fully hereinafter with reference to the accompanying drawings, in which some, but not all embodiments are shown. Indeed, the present disclosure may be embodied in many different forms and should not be construed as limited to the embodiments set forth herein; rather, these embodiments are provided so that this disclosure will satisfy applicable legal requirements. Like numbers refer to like elements throughout.

Cigarette rods are manufactured using a cigarette making machine, such as a conventional automated cigarette rod making machine. Exemplary cigarette rod making machines are of the type commercially available from Molins PLC or Hauni-Werke Korber & Co. KG. For example, cigarette rod making machines of the type known as MIA (commercially available from Molins PLC) or PROTOS (commercially available from Hauni-Werke Korber & Co. KG) can be employed. A description of a PROTOS cigarette making machine is provided in U.S. Pat. No. 4,474,190 to Brand, at col. 5, line 48 through col. 8, line 3, which is incorporated herein by reference. Types of equipment suitable for the manufacture of cigarettes also are set forth in U.S. Pat. No. 4,781,203 to La Hue; U.S. Pat. No. 4,844,100 to Holznagel; U.S. Pat. No. 5,156,169 to Holmes et al.; U.S. Pat. No. 5,191,906 to Myracle, Jr. et al.; U.S. Pat. No. 6,647,870 to Blau et al.; U.S. Pat. No. 6,848,449 to Kitao et al.; U.S. Pat. No. 6,904,917 to Kitao et al.; U.S. Pat. No. 7,210,486 to Hartman; U.S. Pat. No. 7,234,471 to Fitzgerald et al.; U.S. Pat. No. 7,275,548 to Hancock et al.; and U.S. Pat. No. 7,281,540 to Barnes et al.; each of which is incorporated herein by reference.

The components and operation of conventional automated cigarette making machines will be readily apparent to those skilled in the art of cigarette making machinery design and operation. For example, descriptions of the components and operation of several types of chimneys, tobacco filler supply equipment, suction conveyor systems and garniture systems are set forth in U.S. Pat. No. 3,288,147 to Molins et al.; U.S. Pat. No. 3,915,176 to Heitmann et al; U.S. Pat. No. 4,291,713 to Frank; U.S. Pat. No. 4,574,816 to Rudszinat; U.S. Pat. No. 4,736,754 to Heitmann et al. U.S. Pat. No. 4,878,506 to Pinck et al.; U.S. Pat. No. 5,060,665 to Heitmann; U.S. Pat. No. 5,012,823 to Keritsis et al. and U.S. Pat. No. 6,360,751 to Fagg et al.; and U.S. Patent Application Publication No. 2003/0136419 to Muller; each of which is incorporated herein by reference. The automated cigarette making machines of the type set forth herein provide a formed continuous cigarette rod or smokable rod that can be subdivided into formed smokable rods of desired lengths.

Filtered cigarettes incorporating filter elements provided from filter rods can be manufactured using traditional types of cigarette making techniques. For example, so-called "six-up" filter rods, "four-up" filter rods and "two-up" filter rods that are of the general format and configuration conventionally used for the manufacture of filtered cigarettes can be handled using conventional-type or suitably modified cigarette rod handling devices, such as tipping devices available as Lab MAX, MAX, MAX S or MAX 80 from Hauni-Werke Korber & Co. KG. See, for example, the types of devices set forth in U.S. Pat. No. 3,308,600 to Erdmann et al.; U.S. Pat. No. 4,281,670 to Heitmann et al.; U.S. Pat. No. 4,280,187 to Reuland et al.; U.S. Pat. No. 6,229,115 to Vos et al.; U.S. Pat. No. 7,296,578 to Read, Jr.; and U.S. Pat. No. 7,434,585 to Holmes, each of which is incorporated herein by reference. The operation of those types of devices will be readily apparent to those skilled in the art of automated cigarette manufacture.

Various types of cigarette components, including tobacco types, tobacco blends, top dressing and casing materials, blend packing densities; types of paper wrapping materials for tobacco rods, types of tipping materials, and levels of air dilution, can be employed. See, for example, the various representative types of cigarette components, as well as the various cigarette designs, formats, configurations and characteristics, that are set forth in U.S. Pat. No. 5,220,930 to Gentry, U.S. Pat. No. 6,779,530 to Kraker, U.S. Pat. No. 7,237,559 to Ashcraft et al., and U.S. Pat. No. 7,565,818 to Thomas et al. and U.S. Patent Application Publication Nos. 2005/0066986 to Nestor et al., and 2007/0246055 to Oglesby; each of which is incorporated herein by reference.

Filter rods can be manufactured using a rod-making apparatus, and an exemplary rod-making apparatus includes a rod-forming unit. Representative rod-forming units are available as KDF-2, KDF-2E, KDF-3, and KDF-3E from Hauni-Werke Korber & Co. KG; and as Polaris-ITM Filter Maker from International Tobacco Machinery. Filter material, such as cellulose acetate filamentary tow, typically is processed using a conventional filter tow processing unit. For example, filter tow can be bloomed using bussel jet methodologies or threaded roll methodologies. An exemplary tow processing unit has been commercially available as E-60 supplied by Arjay Equipment Corp., Winston-Salem, N.C. Other exemplary tow processing units have been commercially available as AF-2, AF-3 and AF-4 from Hauni-Werke Korber & Co. KG and as Candor-ITM Tow Processor from International Tobacco Machinery. Other types of commercially available tow processing equipment, as are known to those of ordinary skill in the art, can be employed. Other types of filter materials, such as gathered paper, nonwoven polypropylene web or gathered strands of shredded web, can be provided using the types of materials, equipment and techniques set forth in U.S. Pat. No. 4,807,809 to Pryor et al. and U.S. Pat. No. 5,025,814 to Raker. In addition, representative manners and methods for operating a filter material supply units and filter-making units are set forth in U.S. Pat. No. 4,281,671 to Bynre; U.S. Pat. No. 4,850,301 to Green, Jr. et al.; U.S. Pat. No. 4,862,905 to Green, Jr. et al.; U.S. Pat. No. 5,060,664 to Siems et al.; U.S. Pat. No. 5,387,285 to Rivers and U.S. Pat. No. 7,074,170 to Lanier, Jr. et al.

Representative types of filter rods incorporating objects, and representative types of cigarettes possessing filter elements incorporating objects, such as flavor-containing capsules or pellets, can possess the types of components, format and configuration, and can be manufactured using the types of techniques and equipment set forth in U.S. Pat. No. 4,862,905 to Green, Jr. et al.; U.S. Pat. No. 7,115,085 to Deal; U.S. Pat. No. 7,479,098 to Thomas et al.; U.S. Pat. No. 7,740,019 to Nelson et al.; and U.S. Pat. No. 7,972,254 to Stokes et al. and U.S. Patent Application Publication No. 2012/0037546 to Dixon et al., which are incorporated herein by reference in their entireties. See also U.S. Patent Application Publication Nos. 2011/0162662 to Nikolov et al.; 2011/0162665 to Burov et al.; 2012/0077658 to Nikolov et al.; and 2012/0245006 to Henley et al.; and 2012/0245007 to Henley et al., which are incorporated herein by reference in their entireties.

Cigarette filter rods can be used to provide multi-segment filter rods. Such multi-segment filter rods can be employed for the production of filtered cigarettes possessing multi-segment filter elements. An example of a two-segment filter element is a filter element possessing a first cylindrical segment incorporating activated charcoal particles (e.g., a "dalmatian" type of filter segment) at one end, and a second cylindrical segment that is produced from a filter rod, with or without objects inserted therein. The production of multi-segment filter rods can be carried out using the types of rod-forming units that have been employed to provide multi-segment cigarette filter components. Multi-segment cigarette filter rods can be manufactured, for example, using a cigarette filter rod making device available under the brand name Mulfi from Hauni-Werke Korber & Co. KG of Hamburg, Germany.

Figure 1:
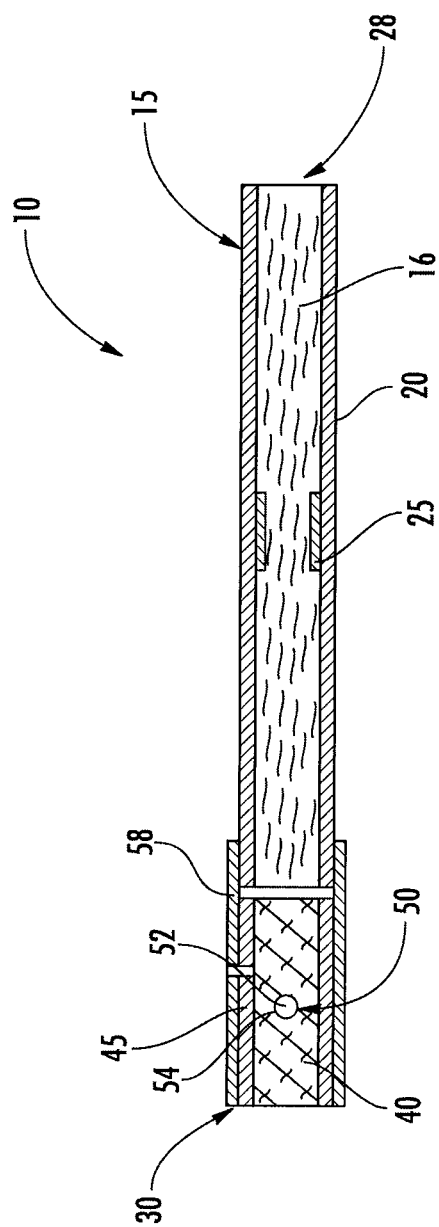
FIG. 1 illustrates a cross-sectional view through a smoking article having the form of a cigarette with an object received in a filter element according to an example embodiment of the present disclosure.

Referring to FIG. 1, there is shown a smoking article 10, such as a cigarette, possessing certain representative components of a smoking article. The cigarette 10 includes a generally cylindrical rod 15 of a charge or roll of smokable filler material 16 contained in a circumscribing wrapping material 20. The rod 15 is conventionally referred to as a "tobacco rod." The ends of the tobacco rod 15 are open to expose the smokable filler material 16. The smoking article 10 is shown as having one optional band 25 (e.g., a printed coating including a film-forming agent, such as starch, ethylcellulose, or sodium alginate) applied to the wrapping material 20, which circumscribes the smokable filler material 16 in a direction transverse to the longitudinal axis of the smoking article. That is, the band 25 provides a cross-directional region relative to the longitudinal axis of the smoking article 10. The band 25 can be printed on the inner surface of the wrapping material 20 (i.e., facing the smokable filler material 16) as shown, or less preferably, on the outer surface of the wrapping material. Although the smoking article 10 can possess a wrapping material having one optional band, the smoking article also can possess wrapping material having further optional spaced bands numbering two, three, or more.

The wrapping material 20 of the tobacco rod 15 can have a wide range of compositions and properties. The selection of a particular wrapping material 20 will be readily apparent to those skilled in the art of smoking article design and manufacture. Tobacco rods can have one layer of wrapping material; or tobacco rods can have more than one layer of circumscribing wrapping material, such as is the case for the so-called "double wrap" tobacco rods. Exemplary types of wrapping materials, wrapping material components and treated wrapping materials are described in U.S. Pat. No. 5,220,930 to Gentry; U.S. Pat. No. 7,275,548 to Hancock et al.; and U.S. Pat. No. 7,281,540 to Barnes et al.; PCT Application Pub. Nos. WO 2004/057986 to Hancock et al. and WO 2004/047572 to Ashcraft et al., each of which is incorporated herein by reference in its entirety.

At one end of the tobacco rod 15 is the lighting end 28, and a filter element 30 is positioned at an opposite end. The filter element 30 is positioned adjacent one end of the tobacco rod 15 such that the filter element and tobacco rod are axially aligned in an end-to-end relationship, preferably abutting one another. The filter element 30 may have a generally cylindrical shape, and the diameter thereof may be essentially equal to the diameter of the tobacco rod 15. The ends of the filter element 30 permit the passage of air and smoke therethrough. The filter element 30 includes filter material 40 (e.g., cellulose acetate tow impregnated with triacetin plasticizer) that is over-wrapped along the longitudinally extending surface thereof with circumscribing plug wrap material 45. That is, the filter element 30 is circumscribed along its outer circumference or longitudinal periphery by a layer of plug wrap 45, and each end of the filter element is open to expose the filter material 40.

The filter element 30 is attached to the tobacco rod 15 using tipping material 58 (e.g., essentially air impermeable tipping paper), that may circumscribe the entire length of the filter element and an adjacent region of the tobacco rod 15. The inner surface of the tipping material 58 is fixedly secured to the outer surface of the plug wrap 45 and the outer surface of the wrapping material 20 of the tobacco rod 15, using a suitable adhesive; and hence, the filter element 30 and the tobacco rod are connected to one another.

Within the filter element 30 may be positioned at least one object 50, and in some instances a plurality of objects 50 (including, for example, capsules, pellets, strands), which can include various combinations of different objects. The number of objects 50 within each filter element 30 is typically a pre-determined number, and that number can be 1, 2, 3, or more (i.e., at least one). In some instances, each filter element 30 contains a plurality of objects 50 disposed within the filter material 40 of the filter element wherein, in further instances, the objects may be particularly disposed toward the central region of the filter element. The nature of the filter material 40 is such that the objects 50 are secured or lodged in place within the filter element 30. In some instances, the object 50 (or some or all of a plurality of the objects) may be hollow, such as a breakable capsule. The object 50 may carry a payload 52 (e.g., a liquid or gel) incorporating a compound (e.g., a flavoring agent) that is intended to introduce some change to the nature or character of mainstream smoke drawn through that filter element 30. That is, a shell 54 of some hollow objects 50 may be ruptured at the discretion of the smoker to release the payload 52. Alternatively, some objects 50 may be a solid, porous material with a high surface area capable of altering the smoke and/or air drawn through the filter element. Some objects may be a solid material, such as a polyethylene bead, acting as a substrate or matrix support for a flavoring agent. Some objects may be capable of releasing the agent at the command of the user. For example, a breakable hollow object containing a liquid payload may be resistant to the release of the payload until the time that the smoker applies a purposeful application of physical force sufficient to rupture the hollow object. Typically, the filter material 40, such as cellulose acetate tow, or an inserted strand, is generally absorbent of liquid materials of the type that comprise the payload 52, and hence the released payload components may be capable of undergoing wicking (or otherwise experiencing movement or transfer) throughout the filter element 30. Since at least one object 50 may be included in each filter element 30, the filter element may include combinations of various types of objects, as appropriate or desired.

The objects 50 can vary. Each object may possess a generally spherical shape, and, in some instances, may be highly spherical in nature. Some objects can be generally solid in nature. Some objects can be composed of a plastic material; and each can be, for example, a solid spherical bead composed of a mixture of polyethylene and flavor, or a spherical bead having the form of exchange resin or gel. Some objects can be composed of an inorganic material; and can be for example, a spherical alumina bead. The objects also can each have the form of a spherical bead composed of a carbonaceous material. The objects also can each have the form of a hollow sphere. Typical hollow objects are liquid-containing objects, such as breakable capsules, which may be highly spherical, may be uniform in size and weight, have surface properties that allow such objects to be processed efficiently and effectively using automated filter making equipment, and are highly uniform in composition. Some objects may have diameters of about 3 mm to about 4 mm, preferably about 3.5 mm, and the components of the preferred filter rod-making equipment of the present disclosure are suitably adapted or designed to efficiently and effectively produce filter rods incorporating those types of objects.

Other types of objects (e.g., beads, pellets, capsules and capsule components) that can be employed for the production of filter rods using the foregoing filter rod manufacturing techniques and equipment are of the type set forth in U.S. Patent Application Publication No. 2011/0271968 to Carpenter et al., which is incorporated herein by reference. Additional examples of objects are included within commercially available filtered cigarettes, such as those that have been marketed under the tradenames "Camel Lights with Menthol Boost," "Camel Crush," "Camel Silver Menthol," "Camel Filters Menthol," and "Camel Crush Bold" by R. J. Reynolds Tobacco Company.

The objects 50 may be attached or otherwise associated with a strand, and the size of a strand of objects can vary, with the diameter thereof being up to about 2.5 mm, or up to about 3 mm, and sometimes up to about 4 mm. However, due to, for example, limitations in the size (diameter) of the filter rod or filter element, larger diameter strands may require smaller dimensions of other objects (i.e., capsules and/or pellets) such that the other objects can be inserted into the filter material with the strand, while providing the desired dimensions of the filter rod or filter element. In some instances, one or more individual strands are inserted into the filter material, in addition to at least one other object such as a capsule or a pellet. In instances of the other objects comprising, for example, a capsule and/or a pellet, and the filter rod also including a strand, the capsules and/or pellets are disposed at predetermined positions within and along the filter rod or filter element, while the strand, if any, extends through the filter rod or filter element.

Figure 2:
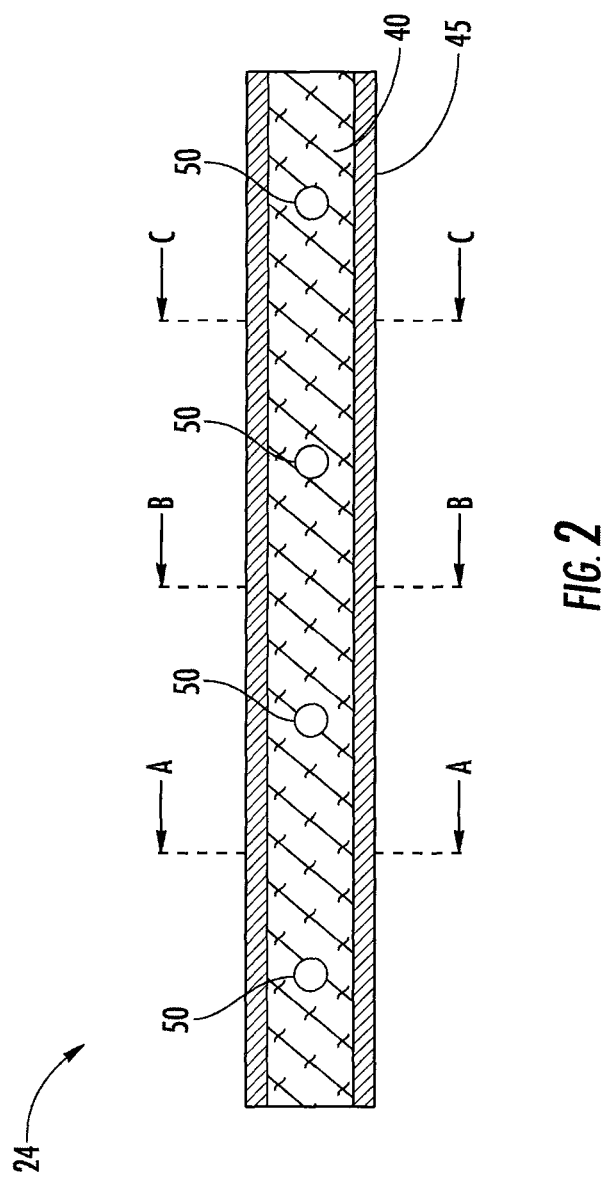
FIG. 2 illustrates a cross-sectional view through a filter rod including filter material and objects positioned therein according to an example embodiment of the present disclosure.

Referring to FIG. 2, a filter rod 24 generally can be subdivided into cylindrical shaped filter elements or rod portions using techniques as are known by the skilled artisan familiar with conventional cigarette manufacturing. The filter rod 24 includes filter material 40 encased in circumscribing wrapping material 45 such as conventional air permeable or air impermeable paper plug wrap, or other suitable wrapping material. As an example, only one object, at least one object 50, or a plurality of objects (shown spaced apart groups for clarity, but essentially adjacent to each other) may be disposed along the longitudinal axis of and within the filter rod 24. Where a plurality of objects 50 is inserted into the filter rod 24, the objects may be disposed in a spaced apart relationship from one another, or immediately adjacent to each other so as to be, in some instances, serially engaged. In other instances (not shown), the objects may be disposed so as to have a repeating pattern of objects or groups of objects (each group comprising one or more objects) separated by a space, wherein the space would correspond to a division between filter rod portions. One skilled in the art will note that the entire filter rod may include sufficient objects therein such that each filter rod portion includes the same number (i.e., one or more) objects when the filter rod is subdivided. For example, a four-up filter rod may include objects in multiples of four such that, upon subdivision, each filter rod portion may include, for example, 1, 2, 3, or 4 objects. In this regard, by way of example, the filter rod 24 illustrated in FIG. 2 may be divided along lines A-A, B-B, and C-C to produce four filter elements 30 each including an object 50 therein.

FIG. 3 illustrates a system for forming smoking articles 200. The system 200 may include a rod-making apparatus 210 configured to produce filter rods 24, each incorporating at least one object, such as spherical, capsular, cylindrical (i.e., pellets), stranded, or other suitably shaped objects. An exemplary rod-making apparatus 210 includes a rod-forming unit 212 (e.g., a KDF-2 unit available from Hauni-Werke Korber & Co. KG) and an object insertion unit 214 suitably adapted to provide for placement of the objects (not shown) within a continuous length of filter material 40. The object insertion unit 214 may be referred to as a capsule insertion unit when configured to insert capsules into the filter material 40. The continuous length or web of filter material 40 is supplied from a source (not shown) such as a storage bale, bobbin, spool or the like.

The filter material 40 can vary, and can be any material of the type that can be employed for providing a tobacco smoke filter for cigarettes. Preferably a traditional cigarette filter material is used, such as cellulose acetate tow, gathered cellulose acetate web, polypropylene tow, gathered cellulose acetate web, gathered paper, strands of reconstituted tobacco, or the like. Especially preferred is filamentary tow such as cellulose acetate, polyolefins such as polypropylene, or the like. One highly preferred filter material that can provide a suitable filter rod is cellulose acetate tow having 3 denier per filament and 40,000 total denier. As another example, cellulose acetate tow having 3 denier per filament and 35,000 total denier can provide a suitable filter rod. As another example, cellulose acetate tow having 8 denier per filament and 40,000 total denier can provide a suitable filter rod. For further examples, see the types of filter materials set forth in U.S. Pat. No. 3,424,172 to Neurath; U.S. Pat. No. 4,811,745 to Cohen et al.; U.S. Pat. No. 4,925,602 to Hill et al.; U.S. Pat. No. 5,225,277 to Takegawa et al. and U.S. Pat. No. 5,271,419 to Arzonico et al.

Generally, the filter material 40 is processed using a filter material processing unit 218, such as a commercially available E-60 supplied by Arjay Equipment Corp., Winston-Salem, N.C. Other types of commercially available tow processing equipment, as are known to those of ordinary skill in the art, may similarly be used. Normally a plasticizer such as triacetin is applied to the filamentary tow in traditional amounts using known techniques. Other suitable materials for construction of the filter element will be readily apparent to those skilled in the art of cigarette filter design and manufacture.

The continuous length of filter material 40 is pulled through a block 230 by the action of the rod-forming unit 212 and the objects are inserted along the length of and within the web of filter material by an object insertion unit 214. However, the objects may also be introduced into the filter material at other points in the process, and this exemplary embodiment is not intended to be limiting in that regard. The object insertion unit 214 may include a rotatable insertion member 248 having the shape of a wheel, which may be positioned so as to rotate in a vertical plane. The object insertion unit 214 may also include a hopper assembly 252 and/or other transfer device for feeding or otherwise providing transfer of objects (such as, for example, capsules and/or pellets) to the insertion member 248. As the insertion member 248 rotates, individual objects (not shown) held within pockets (not shown) on the peripheral face of the wheel are brought into contact with the filter material 40 within the block 230, where the objects are ejected from the pockets into the gathered filter material 40. Details of such an object-insertion arrangement are further detailed, for example, in U.S. Pat. No. 7,115,085 to Deal and U.S. Pat. No. 7,479,098 to Thomas et al.; U.S. Pat. No. 7,740,019 to Nelson et al.; and U.S. Pat. No. 7,972,254 to Stokes et al.

The rate at which the objects are inserted into the continuous web of filter material 40 may be in a direct relationship to the speed of operation of the rod-making apparatus 210. The object insertion unit 214 can be geared in a direct drive relationship to the drive assembly of the rod-making apparatus 210. Alternatively, the object insertion unit 214 can have a direct drive motor synchronized with the drive assembly of the rod-forming unit. In some instances, the object insertion unit 214 may be configured to be in communication with an inspection/detection system (e.g., the inspection detection system 400, described below), for example, in the form of a feedback loop, whereby some defects detected by the inspection/detection system may be eliminated by adjusting the upstream object insertion unit. In light of the relationship of the rate of object insertion and the rod-making apparatus 210, embodiments of the present disclosure are also directed to maintaining or increasing the production rate of the rod-making apparatus, without adversely affecting the object placement within the filter material.

The filter material 40 is further directed into a gathering region 232 of the rod-forming unit 212. The gathering region 232 can have a tongue and horn configuration, a gathering funnel configuration, stuffer or transport jet configuration, or other suitable type of gathering device. The tongue region 232 provides for further gathering, compaction, conversion or formation of the cylindrical composite from block 230 into an essentially cylindrical (i.e., rod-like) shape whereby the continuously extending strands or filaments of the filter material 40 extend essentially along the longitudinal axis of the cylinder so formed. In some instances, the objects may also be placed into the filter material in the gathering region 232, as appropriate.

The filter material 40, which has been compressed into a cylindrical composite, is received further into the rod-forming unit 212. The cylindrical composite is fed into wrapping mechanism 234, which includes endless garniture conveyer belt 236 or other garniture device. The garniture conveyer belt 236 may be continuously and longitudinally advanced using advancing mechanism 238 such as a ribbon wheel or cooperating drum so as to transport the cylindrical composite through wrapping mechanism 234. The wrapping mechanism 234 provides a strip of wrapping material 45 (e.g., non-porous paper plug wrap) to the outer surface of the cylindrical composite in order to produce a continuous wrapped filter rod 220. In some instances, the objects may also be engaged with the filter material in the wrapping or garniture region 232, as appropriate. For example, the elongate member, as otherwise disclosed herein, may be in the form of a wrapping material 45 having the objects attached thereto or otherwise engaged therewith. In some instances, the elongate member may also include, for example, microcapsules (see, e.g., U.S. Patent Application Pub. No. 2008/0142028 to Fagg, incorporated herein by reference) instead of or in addition to the objects, wherein the elongate member/wrapping material is wrapped about the filter material such that the objects/microcapsules are applied thereto.

Generally, the strip or web of wrapping material 45 is provided from rotatable bobbin 242. The wrapping material 45 is drawn from the bobbin, is trained over a series of guide rollers, passes under block 230, and enters the wrapping mechanism 234 of the rod-forming unit. The endless garniture conveyer belt 236 transports both the strip of wrapping material 45 and the cylindrical composite in a longitudinally extending manner through the wrapping mechanism 234 while draping or enveloping the wrapping material about the cylindrical composite.

The seam formed by an overlapping marginal portion of wrapping material has adhesive (e.g., hot melt adhesive) applied thereto at applicator region 244 in order that the wrapping material can form a tubular container for the filter material 40. Alternatively, the hot melt adhesive may be applied directly upstream of the wrapping material's entry into the garniture of the wrapping mechanism 234 or block 230, as the case may be. The adhesive can be cooled using chill bar 246 in order to cause rapid setting of the adhesive. It is understood that various other sealing devices and other types of adhesives can be employed in providing the continuous wrapped rod.

The continuous wrapped filter rod 220 passes from the sealing device and is subdivided (e.g., severed) at regular intervals at the desired, predetermined length using cutting assembly 222 which includes as a rotary cutter, a highly sharpened knife, or other suitable rod cutting or subdividing device. It is particularly desirable that the cutting assembly 222 does not flatten or otherwise adversely affect the shape of the rod. The rate at which the cutting assembly 222 severs the continuous rod at the desired points is controlled via an adjustable mechanical gear train (not shown), or other suitable device. The resulting filter rods 24 can be transported directly to a cigarette making machine or collected for use in a collection device which may be a tray, a rotary collection drum, conveying system, or the like. In such a manner, in excess of 500 filter rods 24, each of about 100 mm length, can be manufactured per minute.

In controlling this process, a control system may include appropriate control hardware and/or software. An exemplary control system 290 can incorporate, for example, a Siemens 315-2DP Processor, a Siemens FM352-5 Boolean Processor and a 16 input bit/16 output bit module. Such a system can utilize a system display 293, such as a Siemens MP370 display. An exemplary rod-making unit 212 may include controls configured, for a rod of desired length, to adjust the speed of the knife of the severing unit to be timed relative to the speed of continuous rod formation. In such instances, an encoder 296, by way of connection with the drive belt of the rod-making unit, and a control unit 299 of the object insertion unit 214, may provide a reference of the knife position of the cutting assembly 222 relative to the wheel position of the insertion unit. Thus, the encoder 296 may provide one manner of controlling the speed of rotation of the wheel of the insertion unit relative to the speed at which continuous web of filter tow passes through the rod-making unit. An exemplary encoder 296 is available as a Heidenhain Absolute 2048 encoder.

The rod-making apparatus 210 can also include a system for providing information associated with rod production and operational analysis. For example, a rod-making apparatus 210, such as a commercially available KDF-2 type unit, can be adapted to include a processing or analysis unit such as, for example, a Siemens 314-C processor. The processing/analysis unit may include associated input and output modules. As such, the processing unit may be configured to monitor the operation of the rod-making apparatus 210 and to collect generated data. The collected data received by the processing unit can then be presented, for example, via a video screen or otherwise transmitted or retrieved via a higher level operating system (e.g., via an Ethernet). For example, a remote data collection unit such as a Siemens IM-153 unit equipped with inputs, outputs and a counter module (available, for example, as a Siemens FM350-2 module), may be installed in a sending unit that receives the collected data from the processing unit via a bus system (e.g., Profibus). Depending upon the particular information gathered, data can be collected relating to, for instance, the number of rods manufactured during a particular time, the machine operating speed, the manufacturing efficiency of the rod-making apparatus, the number of interruptions in the manufacturing process, the number of filter elements provided to the rod-making unit, and any stoppage reasons.

Further, the system 200 may include a cigarette making apparatus 300, as schematically illustrated in FIG. 3. The cigarette making apparatus 300 may attach a tobacco rod 15 wrapped with the wrapping material 20 to a filter rod 24 via tipping material 58. More particularly, a tobacco rod maker 302 may form the tobacco rod 15 by wrapping a wrapping material 20 about smokable filler material 16. Further, a tipping device 304 may attach one or more tobacco rods 15 to the filter rods 24 with tipping material 58 to form, e.g., a combined two-up rod 305. A cutting device 306 may divide the two-up rod 305 into smoking articles 10. Exemplary embodiments of machines that may be employed as the cigarette making apparatus 300 have been described above.

As illustrated in FIG. 3, embodiments of the present disclosure may further include an inspection/detection system 400 for analyzing a smoking article filter. A smoking article filter, as employed herein, refers to a filter which is either part of a smoking article or configured to be included in a smoking article. In this regard, by way of example, smoking article filters include portions of the continuous filter rod 220 (wrapped or unwrapped), filter rods 24 that have been divided, and finished filter elements 30. Thus, the inspection/detection system 400 may analyze smoking article filters at any stage of production of the smoking article filters or the smoking articles as a whole.

The inspection/detection system 400 may determine a filter status of the smoking article filter. As used herein, the term filter status refers to any information regarding the presence, size, shape, integrity (e.g., improperly glued or positioned components), components, composition, and/or properties (e.g., weight) of the smoking article filter as a whole and/or the components thereof and/or any other factor(s) which deem the filter to meet or fail specifications and/or render the smoking article filter commercially acceptable or unacceptable. In this regard, the filter status may relate to the smoking article filter itself in some embodiments. For example, the inspection/detection system 400 may determine whether the filter material 40 is the correct filter material. Thus, the inspection/detection system 400 may compare an expected filter material to a detected filter material. By way of further example, the inspection/detection system 400 may determine whether the smoking article filter is a correct shape. In this regard, filter elements are typically cylindrical. However, in other embodiments filter elements may define alternate shapes. For examples, cigarettes marketed under the tradename "Vantage" by R. J. Reynolds Tobacco Company include a filter element with a conical hole therein. Thus, the inspection/detection system 400 may compare the expected shape of the smoking article filter to a detected shape of the smoking article filter.

In some embodiments the filter status may comprise an object insertion status of an object 50 with respect to the smoking article filter. In this regard, all or a portion of the inspection/detection system 400 may be disposed downstream from the object insertion unit 214 in order to determine the object insertion status. Embodiments of inserted objects include, by way of example, threads, tubes, capsules, etc. For example, an object insertion status may include one or more of an object presence within the filter element, an object absence from the filter element, a proper object (i.e., the desired object), an improper object (i.e., the detected object is not the desired object, for example, a thread is inserted instead of a desired capsule), a proper insertion of an object into the filter element, a defective insertion of an object into the filter element, a proper object within the filter element, and a defective object within the filter element (i.e., object present, but not properly inserted (misaligned), or object present and properly inserted, but is otherwise defective (misshapen, leaking or ruptured)). Accordingly, such an inspection/detection system 400 may be beneficial for identifying defective smoking article filters, or otherwise differentiating acceptable smoking article filters from unacceptable (or defective) smoking article filters.

Such defects in the smoking article filters may include missing objects, misplaced objects, misaligned objects, or, in the case of rupturable (breakable) elements, already ruptured objects. For example, a rupturable element, such as a capsule, may become ruptured or broken during or after insertion into the filter rod or element, while proceeding along the production process for the smoking article. Such a defect may be referred to as an already-broken-capsule ("ABC"). In other instances, the object or objects may be completely missing from the filter rod due to, for example, a malfunctioning object insertion unit 214 used to insert objects into the filter material 40. Still in other instances, the objects 50 may be misplaced, misaligned or mispositioned within the smoking article filter such that, during division of the continuous filter rod 220 into filter rods 24, one or more of the objects may be severed, thereby causing a defect.

The system for forming smoking articles 200 may further comprise a defective smoking article filter removal device 500. The defective smoking article filter removal device 500 may be in communication with the inspection/detection system 400 and configured to remove a defective smoking article filter when the object insertion status determined by the inspection/detection system indicates at least one of an object absence from the smoking article filter, a defective insertion of an object into the smoking article filter, and a defective object within the smoking article filter. Removal of defective smoking article filters may comprise removal of defective smoking articles 10', as illustrated in FIG. 3, in embodiments in which the smoking articles 10 are inspected after formation thereof. However, removal of defective smoking article filters may comprise removal of defective portions of the continuous filter rod 220 (wrapped or unwrapped) or defective filter rods 24 or portions thereof in other embodiments. In this regard, the defective smoking article filter removal device 500 may be positioned at any stage of production or packaging of the smoking article filters or the smoking articles as a whole, downstream of or at the inspection/detection system 400.

In some instances, the inspection/detection system 400 may be implemented in an "on-line" manner along the production process, preferably after the one or more objects have been inserted into the continuous filter rod 220 and/or after the continuous filter rod has been divided into individual filter rods 24 or filter elements 30. As such, the determination of the object insertion status of the smoking article filter may occur during the production process, without adversely affecting (or with reduced or minimal effect on) the throughput of the system for forming smoking articles 200. Alternatively, the inspection/detection system 400 may be implemented in an "off-line" manner separate from the production process. In this manner, the smoking article filters may be removed from or otherwise diverted from the production process for an "off-line" inspection before acceptable smoking article filters are directed back to the smoking article production and/or packaging processes. For example, smoking article filters may be transported pneumatically (known to those of skill in the art as "pea-shooting") to and from the system for forming smoking articles and an inspection/detection system. In any instance, the inspection/detection system 400 may be implemented at any point during the manufacturing process, following the insertion of the one or more objects into the smoking article filters, or after the manufacturing process is complete. Accordingly, in some instances, the final smoking article 10 (including the filter element 30 plus tobacco rod 15) may be inspected, while in other instances, the continuous filter rod 220 or individual filter rods 24 or filter elements 30 may be inspected.

According to one embodiment, the inspection/detection system 400 may be disposed in proximity to the cutting assembly 222 of the rod-making apparatus 210, such as immediately before the cutting assembly. In such instances, the continuous wrapped filter rod 220 proceeds along the rod-making apparatus 210 and is analyzed by the inspection/detection system 400 before or after being divided by the cutting assembly 222. The inspection/detection system 400 is configured to determine and output the object insertion status of the smoking article filter (e.g., the continuous wrapped filter rod 220 and/or the individual filter rods 24) and to direct the pertinent information to the control system 290 and/or the defective smoking article filter removal device 500. Accordingly, any defective smoking article filters (i.e., a smoking article filter for which the object insertion status indicates one of an object absence from the filter element, a defective insertion of an object into the filter element, and a defective object within the filter element) may be identified and thus removed from the manufacturing process before the defect is realized in the smoking article 10 end-product.

In other instances, the inspection/detection system 400 may be disposed further downstream in the manufacturing process, or after the manufacturing process is complete. In this regard, Applicants have determined that objects may be damaged when the tipping device 304 wraps tipping material 58 around the tobacco rods 15 and filter rods 24 or during division of the filter rods 24 into filter elements 30. Thus, by way of example, the inspection/detection system 400 illustrated in FIG. 3 is positioned at the cigarette making apparatus 300 and the defective smoking article filter removal device 500 may be downstream therefrom, although the inspection/detection system and the defective smoking article filter removal device may be positioned at various other locations within, or separate from, the system for forming smoking articles 200.

Accordingly, defective smoking article filters may be appropriately rejected and removed prior to distribution of the end product. Further, to facilitate and enhance overall product quality, multiple inspection/detection systems 400 and/or other multiple measurement schemes may be implemented as a redundancy measure. For example, both an on-line and an off-line inspection/detection system may be implemented in the manufacture of the filter rods 24 and/or the smoking articles 10 in order to provide multiple analyses. That is, inspection/detection systems may be employed during and/or after formation of filter rods 24, during and/or after formation of individual filter elements 30, and/or during and/or after formation of the cigarettes or other smoking articles 10, in on-line and/or off-line processes.

Leakage from rupturable objects may be difficult to detect when employing existing embodiments of inspection/detection systems because the quantity of liquid or gel exiting therefrom may be relatively minor during the manufacturing and packaging processes due to smoking articles being manufactured and then packaged in a relatively short period of time. In this regard, existing embodiments of inspection/detection systems may employ, for example, microwave radiation sensors and/or beta radiation sensors to detect density and/or moisture content of filters. However, the density and moisture content of a filter may not change significantly when a rupturable object is recently ruptured, and thus it may be difficult to detect the broken object. Various other embodiments of sensors disclosed in existing embodiments of inspection/detection systems may also suffer from difficulties with respect to detecting objects broken during the manufacturing process, for which a relatively small quantity of liquid or gel has exited from the object prior to inspecting the filter.

Accordingly, embodiments of the inspection/detection system 400 disclosed herein may be configured to detect freshly ruptured capsules, in addition to determining the various other conditions which may be associated with the filter status, as described above. In this regard, in some embodiments the inspection/detection system 400 may be configured to determine a status of a capsule (e.g., a hollow object which may be filled, for example with a liquid or gel, or empty) with respect to a smoking article filter. Thus, in some embodiments a capsule status determined by the inspection/detection system 400 may comprise at least one of a capsule presence within the smoking article filter, a capsule absence from the smoking article filter, a proper insertion of a capsule into the smoking article filter, a defective insertion of a capsule into the smoking article filter, a proper capsule within the smoking article filter, and a defective capsule within the smoking article filter. However, as noted above, the inspection/detection system 400 may additionally be configured to determine the object insertion status of various other embodiments of objects and/or various other filter statuses.

FIG. 4 illustrates an example embodiment of an inspection/detection system 400. In the illustrated embodiment, the inspection/detection system 400 is inspecting a filter element 30 of a smoking article 10. Accordingly, operation of the inspection/detection system 400 is hereinafter generally described in terms of inspecting a filter element 30 of a smoking article 10. However, it should be understood that the inspection/detection system 400 may be employed to inspect various other embodiments of smoking article filters, as described above.

As illustrated, the inspection/detection system 400 may comprise an emitter 402, a sensor 404, and an analysis unit 406. The emitter 402 may be configured to emit an initial signal 408 toward the filter element 30 for interaction therewith. The sensor 404 may be configured to detect a resultant signal 410 resulting from interaction of the initial signal 408 with the filter element 30. In some embodiments the emitter 402 and the sensor 404 may be configured to receive the filter element 30 therebetween, as illustrated in FIG. 4. Further, the sensor 404 and the emitter 402 may be disposed downstream from the object insertion unit 214, as discussed above. In another example embodiment the sensor 404 and the emitter 402 may be disposed downstream of the tipping device 304 configured to wrap the tipping material 58 around the filter element 30 and the tobacco rod 15.

During operation, the filter element 30 of the smoking article 10 may be received between the sensor 402 and the emitter 404, as illustrated in FIG. 4. First and second mirrors 412, 414 may be employed to respectively direct the initial signal 408 toward the filter element 30 and direct the resultant signal 410 toward the sensor 404. Additionally, a converging lens 416 may be configured to focus the initial signal 408 perpendicularly to a longitudinal axis 418 of the filter element 30 (or at another location being analyzed) and a collimator lens 420 may be configured to substantially straighten the resultant signal 410 such that the sensor 404 may properly interpret the resultant signal. In one embodiment at least one of the converging lens 416 and the collimator lens 418 may comprise polymethylpentene. Use of polymethylpentene may be preferable because polymethylpentene may be transparent to signals in the teraHertz frequency range.

Note that although the inspection/detection system 400 is generally described herein as being configured to transmit a signal through a smoking article filter and receive the signal transmitted therethrough, in other embodiments the inspection/detection system may additionally or alternatively be configured to detect the reflected portion of a signal directed at the smoking article filter. In this regard, an additional or alternative sensor may be positioned on the same side of the smoking article filter as the emitter to detect the reflected signal.

The inspection/detection system 400 may further comprise a movement apparatus 422 configured to at least one of linearly displace the smoking article 10 along the longitudinal axis 418 thereof and rotate the smoking article about the longitudinal axis. In this regard, in the illustrated embodiment a holder 424 is configured to grasp the lighting end 28 of the smoking article 10, although the smoking article may be grasped in other locations and manners. The holder 424 may be rotated by a motor 426, such that the smoking article 10 rotates about the longitudinal axis 418. Further, a cylinder 428 may displace a piston 430 fore and/or aft along the longitudinal axis 418 such that the smoking article 10 also moves along the longitudinal axis. The cylinder 428 and piston 430 may be pneumatically or hydraulically powered in some embodiments. In the illustrated embodiment the cylinder 428 displaces the piston 430, the motor 436, and the holder 424 along the longitudinal axis 418 such that the smoking article 10 is also displaced along the longitudinal axis. However, it should be understood that the movement apparatus 422 may be configured to move the smoking article 10 in other manners. Alternatively, the movement apparatus may displace one or both of the sensor 404 and the emitter 402, while the smoking article 10 remains stationary. In this regard, movement of the smoking article 10 may be relative to the emitter 402 and the sensor 404.

The movement apparatus 422 may produce relative movement between the smoking article 10 and the sensor 404 and the emitter 402 in a number of manners. For example, the movement apparatus 422 may linearly displace the smoking article 10 along the longitudinal axis 418 and rotate the smoking article about the longitudinal axis sequentially. For example, the movement apparatus 422 may move the smoking article 10 along the longitudinal axis 418, rotate the smoking article 10 about the longitudinal axis, and then move the smoking article along the longitudinal axis again (which may be repeated in some embodiments). However, in a preferable embodiment the smoking article 10 may be linearly displaced along the longitudinal axis 418 while the smoking article is rotated about the longitudinal axis. Thereby, points on the smoking article 10 other than those on the longitudinal axis 418 may move along a helical path such that the signals 408, 410 may quickly scan the smoking article. In another embodiment the beam width of the initial signal may be sufficiently wide such that the movement apparatus may only rotate the smoking article.

The initial signal 408 may define a frequency of between about 0.1 teraHertz and about 10 teraHertz. In this regard, Applicants have determined that emitters and sensors configured to operate in the teraHertz spectrum may be able to more precisely determine an object insertion status in certain situations, particularly in terms of determining whether a rupturable object is ruptured, as compared to existing embodiments of inspection/detection systems. In one example embodiment, the initial signal may define an initial signal of about 0.48 teraHertz, which Applicants have employed to determine an object insertion status in some aspects. In some embodiments the emitter 402 and the sensor 404 may comprise a Mini-Z High-Speed (HS) teraHertz time domain spectrometer, as sold by Zomega Terahertz Corp., of East Greenbush, N.Y. However, various other embodiments of emitters 402 and sensors 404 may be employed. Additional spectrometers which may define one or both of the emitter and the sensor are described, by way of example, in U.S. Patent Application Publication No. 2009/0066948 to Karpowicz et al., which is incorporated herein by reference.

The analysis unit 406 may be configured to receive the resultant signal 410 from the sensor 404 and determine a filter status based on the resultant signal. The analysis unit 406 may analyze the resultant signal 410 to determine the object insertion status. By way of example, FIG. 5 illustrates a graph 500 of waveforms associated with employing the inspection/detection system 400. In particular, a reference signal 502 is illustrated, as well as first and second resultant signals 504, 506. In the illustrated example embodiment, the reference signal 502 is a resultant signal associated with transmission of an initial signal through air. The first resultant signal 504 is a resultant signal associated with transmission of the initial signal through a smoking article filter at a position at which there is not an object therein. The second resultant signal 506 is a resultant signal associated with transmission of the initial signal through a smoking filter article at a position at which there is an object therein.

A horizontal axis 508 of the graph 500 illustrates a time delay between the transmission of the initial signal and reception of the signal. A vertical axis 510 of the graph 500 illustrates an amplitude of the signals. In this regard, the analysis unit 406 may be configured to detect at least one of a transmission time of the resultant signal and an amplitude of the resultant signal. Accordingly, the analysis unit 406 may be further configured to determine at least one of a difference between the transmission time of the resultant signal and a transmission time of a reference signal and a difference between the amplitude of the resultant signal and the amplitude of the reference signal.

As illustrated, the reference signal 502 has an amplitude 502a that is greater than the amplitudes 504a, 506a of the first and second resultant signals 504, 506. Further, the amplitude 504a of the first resultant signal 504 is greater than the amplitude 506a of the second resultant signal 506. In this regard, Applicants have determined that resultant signals having relatively smaller amplitudes correspond to resultant signals that have traveled through a greater density of mass (e.g., through an object, as opposed to through a filter element without an object).

Additionally, FIG. 5 shows that the signal time delay 502b of the reference signal 502 is less than the signal time delays 504b, 506b of the first and second resultant signals 504, 506. Further, the signal time delay 504b of the first resultant signal 504 is less than the signal time delay 506b of the second resultant signal 506. In this regard, Applicants have determined that resultant signals having relatively larger signal time delays correspond to resultant signals that have traveled through a greater density of mass (e.g., through an object, as opposed to through a filter element without an object).

FIG. 6 illustrates an additional graph 600 of waveforms associated with employing the inspection/detection system 400. In particular, the reference signal 502 and first and second resultant signals 504, 506 are illustrated. Further, a noise 602 signal is illustrated. The noise signal 602 corresponds to a resultant signal associated with ambient conditions and/or other factors that should be ignored, as it is unrelated to the medium through which the signals are directed. The graph 600 illustrates amplitude on the vertical axis 604 and frequency on the horizontal axis 606.

As previously described, the amplitude 502a of the reference signal 502 is greater than the amplitude 504a of the first resultant signal 504, which is greater than the amplitude 506a of the second resultant signal 506. As further illustrated in FIG. 6, the frequency spectrum 502c of the reference signal 502 is greater than the frequency spectrum 504c of the first resultant signal 504, which is greater than the frequency spectrum 506c of the second resultant signal 506. Further, the maximum frequency 502d of the reference signal 502 is greater than the maximum frequency 504d of the first resultant signal 504, which is greater than the maximum frequency 506d of the second resultant signal 506. In this regard, Applicants have determined that objects in smoking article filters may absorb relatively higher frequency signals and allow a relatively smaller frequency spectrum to travel therethrough.

Accordingly, the inspection/detection system 400 disclosed herein may determine a filter status for a smoking article filter. In this regard, the resultant signal may be compared to a reference signal to determine the filter status. Although the reference signal is generally described above as a resultant signal corresponding to transmission of an initial signal through air, in other embodiments the reference signal may comprise the initial signal itself, or the reference signal may comprise a resultant signal corresponding to transmission of the initial signal through a smoking article filter without an object therein or through a smoking article filter with an object therein. Thus, the difference between the resultant signal and the reference signal, or lack thereof, may be calculated by the analysis unit 406 to determine the filter status. Thus, for example, the difference between the amplitude, signal time delay, frequency spectrum, and/or maximum frequency of the reference signal and the resultant signal may be employed to determine the filter status.

FIG. 7 illustrates an image 700 of a smoking article filter with an intact object 702 filled with liquid or gel positioned in filter material 704 and an image 706 of a smoking article filter with a broken object 708 from which the liquid or gel has leaked in a filter material 710. The vertical axes 712, 714 of the images 700, 706 correspond to an angle of rotation about the longitudinal axis of the smoking article filter, whereas the horizontal axes 716, 718 correspond to a distance along the longitudinal axis of the smoking article filter. The darker areas of the images 700, 706 correspond to relatively greater signal absorption, whereas the whiter areas correspond to relatively greater signal transparency. Note that by imaging the smoking article filters along the longitudinal axis thereof and about the circumference thereof (e.g., through the longitudinal and rotational movements described above), any asymmetry in the object or asymmetry in the placement thereof may be detected.

Graphs 750, 752 of resultant signals corresponding to the smoking article filter with the intact object 702 and the smoking article filter with the broken object 708 are also illustrated in FIG. 7, wherein the vertical axes 754, 756 correspond to amplitude and the horizontal 758, 760 axes correspond to signal time delay. As illustrated in the graph 750, the resultant signal 762 received through the filter material 704 defines a greater amplitude 762a and a smaller time delay 762b as compared to the amplitude 764a and the time delay 764b of the resultant signal 764 received through the filter material and the intact object 702.

Further, as illustrated in the graph 752, the resultant signal 766 received through the filter material 710 defines a greater amplitude 766a and a smaller time delay 766b as compared to the amplitude 768a and the time delay 768b of the resultant signal 768 received through the filter material and the broken object 708. However, the differences between the amplitudes 766a, 768a and the signal time delays 766b, 768b are relatively less as compared to when a signal is directed through an intact object. In this regard, the fluid or gel that has leaked out of the broken capsule 708 may cause the filter material 710 to be relatively less transparent to signals, and may cause the object to be relatively more transparent to signals. Further, by comparing the graphs 750, 752 for the intact object 702 and the broken object 708, one can see that the amplitude 764a of the resultant signal 764 received through the intact object is smaller and the signal time delay 764b is greater as compared to the amplitude 768a and the signal time delay 768b of the resultant signal 768 for the broken object. This occurs because the liquid or gel normally absorbs signals in the intact object 702, but when the liquid or gel drains therefrom, the broken object 708 absorbs less of signals directed therethrough.

FIG. 8 illustrates an image 800 of a smoking article filter with an intact object 802 filled with liquid or gel positioned in filter material 804 and an image 806 of a smoking article filter with a broken object 808 from which the liquid or gel has leaked in a filter material 810. Both of the images 800, 806 were produced using an initial signal having a frequency of about 0.48 teraHertz. The vertical axes 812, 814 of the images 800, 806 correspond to an angle of rotation about the longitudinal axis of the smoking article filter, whereas the horizontal axes 816, 818 correspond to a distance along the longitudinal axis of the smoking article filter. The darker areas of the images 800, 806 correspond to relatively greater signal absorption, whereas the whiter areas correspond to relatively greater signal transparency. Note that by imaging the smoking article filters along the longitudinal axis thereof and about the circumference thereof (e.g., through the longitudinal and rotational movements described above), any asymmetry in the object or the placement thereof may be detected.

Graphs 850, 852 of resultant signals corresponding to the smoking article filter with the intact object 802 and the smoking article filter with the broken object 808 are also illustrated in FIG. 8, wherein the vertical axes 854, 856 correspond to amplitude and the horizontal axes 858, 860 correspond to frequency. As illustrated in the graph 850, the resultant signal 862 received through the filter material 804 defines an amplitude 862a that is greater than the amplitude 864a of the resultant signal 864 received through the filter material and the intact object 802. However, as illustrated in graph 852, the resultant signal 866 received through the filter material 810 defines an amplitude 866a that is substantially similar to the amplitude 868a of the resultant signal 868 received through the filter material and the broken object 808.

FIG. 9 illustrates a graph 900 of the change in the amplitude of a resultant signal 902 through a fluid or gel filled object over time after the object is punctured. The vertical axis 904 illustrates amplitude of the resultant signal 902, and the horizontal axis 906 illustrates time from the puncture of the object. As illustrated, the amplitude of the resultant signal 902 initially increases rapidly. Accordingly, the inspection/detection system 400 disclosed herein may be able to detect a broken object shortly after it breaks.

FIG. 10 illustrates a graph 1000 of the change in the time delay of a resultant signal 1002 through a fluid or gel filled object over time after the object is punctured. The vertical axis 1004 illustrates a time delay of the resultant signal 1002 (time between transmission and reception), and the horizontal axis 1006 illustrates time from the puncture of the object. As illustrated, the time delay of the resultant signal 1002 initially decreases rapidly. Accordingly, the inspection/detection system 400 disclosed herein may be able to detect a broken object shortly after it breaks for this additional reason. In this regard, the majority of fluid or gel diffusion from an object appears to occur within the first few seconds after the object is broken.

Accordingly, the inspection/detection system 400 disclosed herein may determine a filter status. Further, the filter status may be determined shortly after an event or process for which breakage of an object is a concern (e.g., shortly after the tipping device 304 wraps tipping material 58 around the tobacco rods 15 and filter rods 24 or during division of the filter rods 24 into filter elements 30). Accordingly, issues with respect to being unable to identify broken objects shortly after they are broken may be avoided.

In addition to determining the filter status, the analysis unit 406 may also be configured to output an indicium indicative of the filter status. In this regard, the analysis unit 406 may output images of smoking article filters (see, e.g., images 700, 706, 800, 806) or graphs of resultant signals (see, e.g., graphs 500, 600, 750, 752, 850, 852). However, in other embodiments the indicium may more directly describe the filter status, such as by indicating whether or not the filter status is acceptable (e.g., a smoking article filter determined to have an object presence within the filter element, a proper insertion of an object into the filter element, and a proper object within the filter element) or unacceptable (e.g., a smoking article determined to have one or more of an object absence from the filter element, a defective insertion of an object into the filter element, and a defective object within the filter element). In this regard, the filter status may be transmitted to the defective smoking article filter removal device 500, such that defective smoking article filters may be removed when the filter status indicates at least one of an object absence from the smoking article filter, a defective insertion of an object into the smoking article filter, and a defective object within the smoking article filter. As described above, the analysis unit may determine the filter status by determining the difference between the amplitude, signal time delay, frequency spectrum, and/or maximum frequency of the reference signal and the resultant signal. For example, the differences therebetween may be compared to threshold values to determine the filter status.

A related method is also provided. As illustrated in FIG. 11, the method may comprise emitting an initial signal defining a frequency between about 0.1 teraHertz to about 10 teraHertz toward a smoking article filter at operation 1100. Further, the method may include detecting a resultant signal resulting from interaction of the initial signal with the smoking article filter at operation 1102. The method may additionally include determining insertion capsule status based on the resultant signal at operation 1104. The method may also include outputting an indicium indicative of the capsule status at operation 1106.

In some embodiments, the frequency of the initial signal may be about 0.48 teraHertz. Also, determining the capsule status at operation 1104 may comprise at least one of determining a transmission time of the resultant signal and determining an amplitude of the resultant signal. Determining the capsule status at operation 1104 may further comprise at least one of determining a difference between the transmission time of the resultant signal and a transmission time of a reference signal and determining a difference between the amplitude of the resultant signal and the amplitude of the reference signal. Additionally, in some embodiments the capsule status may comprise at least one of an object presence within the smoking article filter, an object absence from the smoking article filter, a proper insertion of an object into the smoking article filter, a defective insertion of an object into the smoking article filter, a proper object within the smoking article filter, and a defective object within the smoking article filter.

In some embodiments the method may further comprise inserting an object into the smoking article filter at operation 1108. Additionally, the method may include wrapping a tipping material around the smoking article filter and a tobacco rod at operation 1110. Emitting the initial signal at operation 1100 and detecting the resultant signal at operation 1102 occur after inserting the object into the smoking article filter at operation 1108 and wrapping the tipping material around the smoking article filter and the tobacco rod at operation 1110.

The method may also include positioning the smoking article filter between the sensor and the emitter at operation 1112. The method may further comprise focusing the initial signal perpendicularly to a longitudinal axis of the smoking article filter at operation 1114. Additionally, the method may include at least one of linearly displacing the smoking article filter along a longitudinal axis thereof and rotating the smoking article filter about the longitudinal axis at operation 1116. The method may also include straightening the resultant signal at operation 1118. Further, the method may include removing a defective smoking article filter at operation 1120 when the capsule status indicates at least one of an object absence from the smoking article filter, a defective insertion of an object into the smoking article filter, and a defective object within the smoking article filter.

Many modifications and other embodiments of the present disclosure set forth herein will come to mind to one skilled in the art to which the present disclosure pertains having the benefit of the teachings presented in the foregoing descriptions and the associated drawings. Therefore, it is to be understood that the present disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system, comprising:
    an emitter and a sensor configured to receive a smoking article filter therebetween,
        the emitter being configured to emit an initial signal, the initial signal having a frequency between about 0.1 teraHertz and about 10 teraHertz, toward the smoking article filter;
        the sensor being configured to detect a resultant signal resulting from interaction of the initial signal with the smoking article filter while traveling therethrough;
    a movement apparatus configured to linearly displace the smoking article filter along a longitudinal axis thereof and simultaneously rotate the smoking article filter about the longitudinal axis relative to the sensor and the emitter while the emitter emits the initial signal; and
    an analysis unit configured to receive the resultant signal from the sensor, determine a filter status based on the resultant signal, and output an indicium indicative of the filter status.

2. The system of claim 1, further comprising a converging lens configured to focus the initial signal perpendicularly to the longitudinal axis of the smoking article filter and a collimator lens configured to substantially straighten the resultant signal.

3. The system of claim 1, wherein at least one of the converging lens and the collimator lens comprises polymethylpentene.

4. The system of claim 1, wherein the analysis unit is configured to determine at least one of a transmission time of the resultant signal and an amplitude of the resultant signal.

5. The system of claim 4, wherein the analysis unit is further configured to determine at least one of a difference between the transmission time of the resultant signal and a transmission time of a reference signal and a difference between the amplitude of the resultant signal and the amplitude of the reference signal.

6. The system of claim 1, wherein the frequency of the initial signal is about 0.48 teraHertz.

7. The system of claim 1, wherein the filter status comprises at least one of a capsule presence within the smoking article filter, a capsule absence from the smoking article filter, a proper insertion of a capsule into the smoking article filter, a defective insertion of a capsule into the smoking article filter, a proper capsule within the smoking article filter, and a defective capsule within the smoking article filter.

8. The system of claim 1 further comprising a rod-making apparatus including a capsule insertion unit configured to insert a capsule into the smoking article filter, wherein the sensor and the emitter are disposed downstream from the capsule insertion unit.

9. The system of claim 8, wherein the sensor and the emitter are disposed downstream of a tipping device configured to wrap a tipping material around the smoking article filter and a tobacco rod.

10. The system of claim 1 further comprising a defective smoking article filter removal device in communication with the analysis unit and configured to remove a defective smoking article filter when the filter status indicates at least one of a capsule absence from the smoking article filter, a defective insertion of a capsule into the smoking article filter, and a defective capsule within the smoking article filter.

11. A method, comprising:
   positioning a smoking article filter between a sensor and an emitter;
   emitting an initial signal having a frequency between about 0.1 teraHertz and about 10 teraHertz toward the smoking article filter with the emitter;
   linearly displacing the smoking article filter along a longitudinal axis thereof;
   rotating the smoking article filter about the longitudinal axis simultaneously with linearly displacing the smoking article filter while emitting the initial signal;
   detecting a resultant signal resulting from interaction of the initial signal with the smoking article filter while traveling therethrough with the sensor;
   determining a filter status based on the resultant signal; and
   outputting an indicium indicative of the filter status.

12. The method of claim 11, further comprising focusing the initial signal perpendicularly to the longitudinal axis of the smoking article filter; and
   straightening the resultant signal.

13. The method of claim 11, wherein determining the filter status comprises at least one of determining a transmission time of the resultant signal and determining an amplitude of the resultant signal.

14. The method of claim 13, wherein determining the filter status further comprises at least one of determining a difference between the transmission time of the resultant signal and a transmission time of a reference signal and determining a difference between the amplitude of the resultant signal and the amplitude of the reference signal.

15. The method of claim 11, wherein the frequency of the initial signal is about 0.48 teraHertz.

16. The method of claim 11, wherein the filter status comprises at least one of a capsule presence within the smoking article filter, a capsule absence from the smoking article filter, a proper insertion of a capsule into the smoking article filter, a defective insertion of a capsule into the smoking article filter, a proper capsule within the smoking article filter, and a defective capsule within the smoking article filter.

17. The method of claim 11, further comprising inserting a capsule into the smoking article filter,
   wherein emitting the initial signal and detecting the resultant signal occur after inserting the capsule into the smoking article filter.

18. The method of claim 17, further comprising wrapping a tipping material around the smoking article filter and a tobacco rod,
   wherein emitting the initial signal and detecting the resultant signal occur after wrapping the tipping material around the smoking article filter and the tobacco rod.

19. The method of claim 11, further comprising removing a defective smoking article filter when the filter status indicates at least one of a capsule absence from the smoking article filter, a defective insertion of a capsule into the smoking article filter, and a defective capsule within the smoking article filter.

* * * * *